(12) United States Patent
Epstein

(10) Patent No.: US 10,624,873 B2
(45) Date of Patent: *Apr. 21, 2020

(54) COMPOUNDS AND FORMS OF TREATMENT FOR FEMALE SEXUAL DISORDERS

(71) Applicant: Wendy Anne Epstein, Nyack, NY (US)

(72) Inventor: Wendy Anne Epstein, Nyack, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/680,181

(22) Filed: Aug. 17, 2017

(65) Prior Publication Data
US 2017/0340602 A1    Nov. 30, 2017

Related U.S. Application Data

(63) Continuation of application No. 15/074,984, filed on Mar. 18, 2016, now Pat. No. 9,750,716.

(60) Provisional application No. 62/177,605, filed on Mar. 19, 2015, provisional application No. 62/231,345, filed on Jul. 2, 2015.

(51) Int. Cl.
| | | |
|---|---|---|
| *A61K 31/353* | (2006.01) | |
| *A61P 43/00* | (2006.01) | |
| *A61P 15/02* | (2006.01) | |
| *A61P 15/00* | (2006.01) | |
| *A61K 9/00* | (2006.01) | |
| *A61K 31/085* | (2006.01) | |
| *A61K 31/355* | (2006.01) | |
| *A61K 31/375* | (2006.01) | |
| *A61K 31/565* | (2006.01) | |
| *A61K 31/566* | (2006.01) | |

(52) U.S. Cl.
CPC .......... *A61K 31/353* (2013.01); *A61K 9/0034* (2013.01); *A61K 31/085* (2013.01); *A61K 31/355* (2013.01); *A61K 31/375* (2013.01); *A61K 31/565* (2013.01); *A61K 31/566* (2013.01); *A61P 15/00* (2018.01); *A61P 15/02* (2018.01); *A61P 43/00* (2018.01)

(58) Field of Classification Search
CPC .................................................. A61K 31/353
See application file for complete search history.

(56) References Cited

U.S. PATENT DOCUMENTS

| | | | |
|---|---|---|---|
| 4,675,189 | A | 6/1987 | Kent et al. |
| 5,795,911 | A | 8/1998 | Cheng et al. |
| 5,968,973 | A | 10/1999 | Cheng et al. |
| 6,197,808 | B1 | 3/2001 | Cheng |
| 6,210,679 | B1 | 4/2001 | Bailey |
| 7,790,905 | B2 | 9/2010 | Tawa et al. |
| 7,858,662 | B2 | 12/2010 | Chang |
| 8,669,292 | B2 | 3/2014 | Godin |
| 9,028,890 | B2 | 5/2015 | Ferrari et al. |
| 9,750,716 | B2 | 9/2017 | Epstein |
| 2001/0008891 | A1 | 7/2001 | Subbiah |
| 2002/0151506 | A1 | 10/2002 | Castillo et al. |
| 2003/0105132 | A1 | 6/2003 | Challenger et al. |
| 2004/0053898 | A1 | 3/2004 | Fritzemeier et al. |
| 2004/0137081 | A1 | 7/2004 | Rohdewald et al. |
| 2004/0198706 | A1 | 10/2004 | Carrara et al. |
| 2005/0244520 | A1 | 11/2005 | Thompson et al. |
| 2005/0266121 | A1 | 12/2005 | Lines et al. |
| 2005/0272825 | A1 | 12/2005 | Blom et al. |
| 2006/0134235 | A1 | 6/2006 | Takagaki |
| 2007/0060653 | A1 | 3/2007 | Thompson |
| 2008/0167360 | A1 | 7/2008 | Fang et al. |
| 2011/0129546 | A1 | 6/2011 | Mill |
| 2013/0164394 | A1 | 6/2013 | Ferrari et al. |
| 2013/0210867 | A1 | 8/2013 | Stofman |
| 2014/0315995 | A1 | 10/2014 | Dreher |
| 2016/0271102 | A1 | 9/2016 | Epstein |

FOREIGN PATENT DOCUMENTS

| | | |
|---|---|---|
| CN | 101254206 A | 9/2008 |
| EP | 2179722 B1 | 4/2010 |
| EP | 2585088 B1 | 6/2014 |
| JP | 2005289884 A1 | 10/2005 |
| WO | WO2004062680 A1 | 7/2004 |
| WO | WO2009053932 A1 | 4/2009 |
| WO | WO2011161655 A1 | 12/2011 |
| WO | WO2016098112 A1 | 6/2016 |
| WO | WO2016149675 A1 | 9/2016 |
| WO | WO2018156960 A1 | 8/2018 |

OTHER PUBLICATIONS

Juan et al., Green tea catechins decrease oxidative stress in surgical menopause-induced overactive bladder in a rat model, 2012, BJU International, 110, E236-E244 (Year: 2012).*
Domoney, C., Treatment of vaginal atrophy, 2014, Women's Health, 10(2), pp. 191-200 (Year: 2014).*
Bianchi et al., Photodegradation of (−)-epigallocatechin-3-gallate in topical cream formulations and its photostabilization, 2011, Journal of Pharmaceutical and Biomedical Analysis, 56, pp. 692-697 (Year: 2011).*
Gonzalez-Garrido, JA. "Influence of the AT2 receptor on the L-arginine-nitric oxide pathway and effects of (−)-epicatechin on HUVECs from women with preeclampsia," Journal of Human Hypertension (2013) 27, 355-361; doi:10.1038/jhh.2012.55; published online Dec. 6, 2012.

(Continued)

*Primary Examiner* — Jeffrey S Lundgren
*Assistant Examiner* — Tori Strong
(74) *Attorney, Agent, or Firm* — Kaplan IP Law, P.C.; Jonathan M. Kaplan

(57) ABSTRACT

The invention provides safe and efficacious treatments for Female Sexual Disorders, genitopelvic pain/penetration disorders; vulvovaginal atrophy, vestibulodynia, dyspareunia, sexual interest/arousal disorder, low female libido, and female orgasmic disorder.

20 Claims, 10 Drawing Sheets

(56) References Cited

OTHER PUBLICATIONS

Simon W. Rabkin Can. J. Physiol. Pharmacal. 74: 125-131 (1996). The angiotensin II subtype 2 (AT2) receptor is linked to protein kinase C but not cAMP-dependent pathways in.

Stephanie Dal-Ros, Chronic intake of red wine polyphenols . . . Biochemical and Biophysical Research Communications 404 (2011) 743-749.

Maree T Smith† & Arjun Muralidharan Targeting angiotensin II type 2 receptor pathways to treat neuropathic pain and inflammatory pain Expert Opin.Ther. Targets (2015) 19(1).

Ji Min Kim • Yohei Uehara • Yeon Ja Choi • Young Mi Ha • Byeong Hyeok Ye • Byung Pal Yu • Hae Young Chung Mechanism of . . . Biogerontology(2011) 12:537-550.

Robinder S. Garcha, 1Peter S. Sever & 1Alun D. Hughes Mechanism of action of angiotensin II in human isolated . . . British Journal of Pharmacology (2001) 134, 188+/− 196.

Li, et al Inhibitory effects of catechin compounds on renin activity Biomedical Research vol. 34 (3) pp. 167-171, 2013.

JA Gonza Lez-Garrido Chem et al Influence of the AT2 receptor on the L-arginine-nitric oxide pathway and effects . . . Journal of Human Hypertension (2013) 27, 355-361.

P.Tympanidis,* G.Terenghi and P.Dowd Increased innervation of the vulval vestibule in patients with vulvodynia British Journal of Dermatology 2003; 148: 1021-1027.

Chakrabarty, Audrey Blacklock, Stanislav Svojanovsky, and Peter G. Smith Estrogen Elicits Dorsal . . . Endocrinology. Jul. 2008; 149(7): 3452-3460. Published online Apr. 3, 2008.

Ming Li1, et al Epigallocatechin-3-gallate inhibits angiotensin II and interleukin-6-induced C-reactive protein production in . . . PharmacologicalReports (2012) ,64, 912, 918.

Dennis J. Stuehr Enzymes of the L-Arginine to Nitric Oxide Pathway J. Nutr. 134: 2748S-2751S, 2004.

Kuang, et al. Effects of Intrathecal Epigallocatechin gallate, an inhibitor of Toll-like receptor 4 . . . European Journal of Pharmacology 676 2012 pp. 51-56.

Ingrid A.-L. Persson, Martin Josefsson, Karin Persson and Rolf G. G. Andersson Tea flavanols . . . Pharmacy and Pharmacology 2006, 58: 1139-1144.

Pessoa et al Angiotensin II Type 2 Receptor- and Acetylcholine-Mediated Relaxation Essential Contribution of Female . . . (Hypertension. 2015; 66:396-402.

Girasole AE et al Angiotensin II potentiates adrenergic and muscarinic modulation of guinea pig . . . Am J Physiol Regul Integr Comp Physiol. Nov. 2011;301(5):R1391-9.

Arjun Muralidharan PhD,*† Bruce D. Wyse, PhD,*† and Maree T. Smith, PhDAnalgesic Efficacy and Mode of Action of a Selective . . . Pain Medicine 2014; 15: 93-110.

Helen E. O'Connell, Anatomy of the Clitoris, The Journal of Urology, vol. 174, Oct. 2005, pp. 1189-1195.

Jeong Il Choi, Kim WM, Lee HG, Kim YO, Yoon MH.) . . . Role of neuronal nitric oxide synthase in the antiallodynic effects of intratheca . . . Neurosci Lett. Feb. 1, 2012;510(1):53-7.

Marion Man-Ying Chan, Inhibition of Inducible Nitric Oxide . . . Biochemical Pharmacology, vol. 54, (1997), pp. 1281-1286.

Xie Y, et at.: Economic burden and quality of life of vulvodynia in the United States, Curr. Med Res. Opin 28: 601-608, 2012.

Kao et al, Biopsychological predictors of postmenopausal dyspareunia: the role of steroid hormones, vulvovaginal atrophy, cognitive-emotional . . . J. Sex. Med 2012; 9:2066-76.

Goetsch, et al Locating Pain in Breast Cancer Survivors Experiencing Dyspareunia Obstetrics and Gynecology vol. 123, No. 6. Jun. 2014. pp. 1231-1236.

Leclair, M. Goetsch, H. Li and T. Morgan Histopathologic Characteristics of Menopausal Vestibulodynia) Obstetrics & Gynecology vol. 122, No. 4, Oct. 2013: pp. 787-793.

Leclair, CM, Goetsch, et al Differences in Primary Compared with Secondary Vestibulodynia . . . Obstetrics & Gynecology vol. 117, 2011: 1307-1307-13.

Smith MT, Woodruff TM, Wyse BD, Muralidharan A, Walther T. A small molecule angiotensin II type 2 receptor (AT2R) antagonist produces . . . Pain Med Jun. 6, 2013.

L. Packer, Antioxidant Activity and Biologic . . . Free Radical Biology & Medicine, vol. 27, Nos. 5/6 (1999), pp. 704-724.

Noel N. Kim, Role of Arginase in the Male and Female Sexual Arousal Response, Journal of Nutrition 134: 2873S-2879S (2004).

H. Tapiero, Dossier: Free amino acids in human health and pathologies, I. Arginine, Biomed Pharmacother 56 (2002) pp. 439-445.

Goodin et al Estrogen Receptor Mediated Actions of Polyphenolic Catechins in Vivo and in Vitro Toxicological Sciences 69; 354-361, 2002.

Stefan Uckert, PhDet al Expression and Distribution of Cyclic AMP- and Cyclic GMP-Binding Protein Kinases in the Human Vagina . . . J Sex Med 2010; 7: 888-895.

Gokce Taner, Assessmentof the cytotoxic, genotoxic, and anti-genotoxic . . . Food and Chemical Toxicology 61 (2013) pp. 203-208.

Abdulmaged M. Traish, Biochemical Factors Modulating Female Genital Sexual Arousal Physiology, J Sex Med 2010; 7:2925-2946.

Goestch, M Postpartum dyspareunia Journal of Reproductive Medicine vol. 44 No. 11,1999.

Kao et al Dyspareunia in postmenopausal women: A critical review. Pain Res. Manage. 2008;13(3): 243-254.

Somers-Edgar, et al. The combination of epigallocatechin gallate and curcumin suppresses ER alpha-breast cancer . . . Int J Cancer. May 1, 2008;122(9):1966-71.

Paterson et al Pleasure and Pain: The Effect of (Almost) Having an Orgasm on Genital and Nongenital Sensitivity: J. Sex Med 2013; 10:1531-1544.

Facelle TM, Sadeghi-Nejad H, and Goldmeier D. Persistent genital arousal disorder: Characterization, etiology, and management. J Sex Med 2013;10:439-450.

Alison Amsterdam et al Persistent Sexual Arousal Syndrome Associated with Increase Soy Intake J Sex Med 2005; 2: 338-340.

Philippsohn S1, Kruger TH et al Persistent genital arousal disorder: successful treatment with duloxetine and pregabalin in two cases. J Sex Med. Jan. 2012;9(1):213-7.

Pooja Bhardwaj, Catechin Averts Experimental Diabetes Mellitus-Induced Vascular Endothelial . . . Cardiovasc Toxicol (2014) 14:41-51.

Bell C, Richardson D, Goldmeier D, Crowley T, Kocsis A, Hill S. Persistent sexual arousal . . . Int J Std Aids 2007;18:130-1.

Waldinger MD, Venema PL, van Gils APG, deLint GJ, Schweitzer DH. Stronger evidence for small-fiber sensory neuropathy . . . J Sex Med 2011; 8:325-30.

Korda J, Pfaus J, Goldstein I. Persistent genital arousal disorder: A case report of in a woman with ifelong PGAD . . . J Sex Med 2009;6:1479-86.

Jutta Giesecke et al. Quantitative Sensory Testing in Vulvodynia Patients and Increased Peripheral Pressure Pain . . . Obstet Gynecol 2004;vol. 104, No. 1, Jul. 2004 pp. 126-133.

Jaroenpom el al Improvements of Vaginal Atrophy without Systemic Side Effects after Topical Application . . . J Reprod Dev. Jun. 2014; 60(3): 238-245.

Walter E. Marchand, M.D Analgesic Effect of Masturbation As a Clinical Sign of Painful Somatic Disorders in Psychotic Patients . . . Arch Gen Psychiatry. 1961:4(2):137-138.

Reed BD; Crawford, S; Couper, M; Cave, C (2004). "Pain at the vulvar vestibule: a web-based survey.". Journal of Lower Genital Tract Disease. 8 (1): 48-57.

Barnea ER, MacLusky NJ, DeCherney AH, Naftolin F. Catechol-o-methyl transferase activity in the human term placenta. Am J Perinatol. 1988 5(2):121-7.

Barnea ER, Naftolin F. Estrogen and catechol amine metabolism: possible interaction during pregnancy. J Endocrinol Invest. Jun. 1987;10(3):329-40.

Zhu BT, Patel UK, Cai MX, Conney AH. O-Methylation of tea polyphenols catalyzed by human placental cytosolic catechol- . . . Drug Metab Dispos. 2000 28(9):1024-30.

Mitsumasa Ohyanagi Differential Activation of α1- and v2-Adrenoceptors on Microvascular Smooth Muscle During Sympathetic Nerve . . . (Circulation Research 1991;68:232-244).

(56) References Cited

OTHER PUBLICATIONS

S.K. Segall et al Janus Molecule I: Dichotomous Effects of COMT in Neuropathic vs Nociceptive Pain Modalities CNS Neurol Disord Drug Targets . May 2012 ; 11(3): 222-235.
Jennifer L. Donovan, Catechin is Present as Metabolites in Human Plasma after Consumption . . . J. Nutr. 129: 1662-1668, (1999).
Nina Bohm-Starke et al Increased Blood Flow and Erythema in the Posterior Vestibular Mucosa in Vulvar Vestibulitis vol. 98, No. 6, Dec. 2001 Obstet Gynecol.
Pei Chen, Chromatographic Fingerprint Analysis of Pycnogenol . . . Journal of AOAC International, vol. 92, No. 2, 2009.
Yamagata, Dietary polyphenols regulate endothelial function and prevent . . . Nutrition 31 (2015) 28-37.
Helen E. O'Connell*,† and John O. L. Delancey Clitoral Anatomy in Nulliparous, Healthy, Premenopausal Volunteers Using Unenhanced . . . J Urol. Jun. 2005; 173(6): 2060-2063.
M. A. Weber & J. Limpens & J. P. W. R. RooversAssessment of vaginal atrophy: a review Int Urogynecol J (2015) 26:15-28.
McEndree, B Clinical Application of Vaginal Maturation Index The Nurse Practitioner vol. 24 No. 9 pp. 48-56 1999.
Management of symptomatic vulvovaginal atrophy: 2013 position statement of The North . . . The Journal of The North American Menopause Society vol. 20, No. 9, pp. 888/902 2013.
Kristin Landis-Piwowar et al Novel epigallocatechin gallate analogs as potential anticancer . . . (2009-present Expert Opin Ther Pat . Feb. 2013; 23(2) 2013.
Angela J. Yoon, DDS et al Topical Application of Green Tea Polyphenol (−)Epigallocatechin-3-gallate (EGCG) for Prevention . . . J Orofac Sci. 2012; 4(10): 43-50.
Santo Scalia* Valentina Trotta In vivo human skin penetration of (−)-epigallocatechin-3-gallate from topical formulations Acta Pharm. 64 (2014) 257-265.
Uhlenhut, Facilitated cellular uptake and suppression of inducible . . . Free Radical Biology and Medicine vol. 53 (2012) pp. 305-313.
Drug Patent Watch Database, info on patents with free drug trial, thinkBiotech LLC, Copyright 2002-2017, ISSN: 2162-2639.
T. Nakagawa, Direct scavenging of nitric oxide and superoxide by green tea, Food and Chemical Toxicology 40 (2002) 1745-1750.
Kathryn M Greven, Effect of ArginMax on sexual functioning and quality of life among female . . . J Community Support Oncol., Mar. 2015; 13(3):87-94.
Kohama T, Effect of low-dose French maritime pine bark extract on climacteric . . . J Reprod Med, Jan.-Feb. 2013, 58(1-2):39-46.
Luis Cesar F. Spessoto, Effect of systemic arterial pressure on erectile dysfunction in the initial stages . . . 2010 BJU International, 106: 1723-1725.
Jia-Yi Dong, Effect of oral L-arginine supplementation on blood pressure: A meta-analysis of randomized . . . Am Hear J 2011; 162: 959-65.
Ulrich Forstermann, Endothelial Nitric Oxide Synthase in Vascular Disease . . . Circulation. 2006; 113: 1708-1714.
Mario Lorenz, Endothelial NO Production is Mandatory for Epigallocatechin-3-Gallate- . . . J Cardiovasc Pharmacol (TM) 2015;65:607-610.
Tony J. Verbeuren, Evidence for Induction of Nonendothelial NO . . . Journal of Cardiovascular Pharmacology, 21:841-845 (1993).
Kuei-Meng Wu, Regulatory science: a special update from the United States Food and Drug . . . Toxicology Letters 111 (2000) 199-202.
Salahuddin Ahmed, Green Tea Polyphenol Epigallocatechin-3-Gallate . . . Free Radical Biology & Medicine, vol. 33, No. 8 (2002), pp. 1097-1105.
Arthur L. Burnett, Immunohistochemical Description of Nitric Oxide Synthase Isoforms . . . The Journal of Urology, vol. 158, Jul. 1997, pp. 75-78.
Fengjuan Li, Inhibitory effect of catechin-related compounds on renin activity, Biomedical Research 34 (3) pp. 167-171, 2013.
Bottari A, Lady Prelox (R) improves sexual function in generally healthy women . . . Minerva Ginecol, Aug. 2013; 65(4): 435-44.
Yuyan Xiong, Long term exposure to L-arginine accelerates endothelial cell senescence . . . AGING, May 2014, vol. 6, No. 5.
Green Tea, Natural Medicines Comprehensive Database, Stockton, CA, ww.naturaldatabase.com.
Kazem M. Azadzoi, Neurologic Factors in Female Sexual Function and Dysfunction, Korean Journal of Urology, 2010; 51:443-449.
Francois Giuliano, Neurophysiology and Pharmacology of Female Genital Sexual Response, Journal of Sex & Marital Therapy, (2002), 28(s):101-121.
Arthur L. Burnett, Nitric Oxide in the Penis: Physiology and Pathology, The Journal of Urology, vol. 157, Jan. 1997, pp. 320-324.
Noboru Toda, Nitric oxide and penile erectile function, Pharmacology & Therepeutics 106 (2005) pp. 233-266, Science Direct, Elsevier Inc.
Wendy K. Alderton, Nitric oxide synthases: structure, function and inhibition, Biochem J. (2001) 357, pp. 593-615.
Rebecca L. Drieling, No Beneficial Effects of Pine Bark Extract on . . . Arch Intern Med, vol. 170 (No. 17), Sep. 27, 2010, pp. 1541-1547.
Anne Marie Fine, Oligomeric Proanthocyanidin Complexes: History, Structure . . . Alternative Medicine Review, (2000) vol. 5, No. 2, pp. 144-151.
Tanja Grimm, Single and multiple dose pharmacokinetics of maritime pine bark extract . . . BMC Clinical Pharmacology 2006, 6:4.
Christopher F. Barnett, Pharmacokinetic, partial pharmacodynamic and initial safety analysis . . . Food Funct. Mar. 11, 2015, 6(3): 824-833.
H-H. Sherry Chow, Phase I Pharmacokinetic Study of Tea Polyphenols . . . Cancer Epidemiology, Biomarkers & Prevention, vol. 10, Jan. 2001, pp. 53-58.
Brett Shand, Pilot Study on the Clinical Effects of Dietary . . . Phytotherapy Research 17, 490-494 (2003), Wiley InterScience.
Cadiz-Gurrea, Pine Bark and Green Tea Concentrated Extracts: Antioxidant Activity . . . Int. J. Mol. Sci. 2014, 15, 20382-20402.
Stanislava Jankyova, Glucose and blood pressure lowering effects . . . Pathology-Research and Practice 208 (2012); 452-457.
Gabriele D'Andrea, Pycnogenol: A blend of procyanidins with multifaceted . . . Fitoterapia 81 (2010) 724-736, Science Direct, Elsevier, Inc.
Bo Gao, Pycnogenol Protects Against Rotenone-Induced Neurotoxicity . . . DNA and Cell Biology, vol. 34, No. 10, 2015, pp. 643-649.
Ximing Liu, Antidiabetic effect of Pycnogenol (R) French maritime pine bark . . . Life Sciences 75 (2004) pp. 2505-2513, Science Direct, Elsevier, Inc.
You Jung Kim, Pycnogenol modulates apoptosis by suppressing . . . Food and Chemical Toxicology 49 (2011) pp. 2196-2201, Science Direct, Elsevier, Inc.
Kay CD, Relative impact of flavonoid composition, dose and structure . . . Mol Nutr Food Res. Nov. 2012; 56(11): 1605-16.
Corina Schoen, Sildenafil citrate for female sexual arousal disorder: a future possibility?, G. Nat. Rev. Urol. 6, 216-222 (2009).
Jinglian Yan, Tetrahydrobiopterin, L-Arginine and Vitamin C Act Synergisticallly to Decrease . . . Molecular Medicine 18: 676-684, 2012.
Cyril Auger, The EGCg-induced redox-sensitive . . . Biochemical and Biphysical Research Communications 393 (2010) 162-167.
Cyril Auger, The red wine extract-induced activation of endothelial nitric oxide synthase . . . Mol. Nutr. Food Res. 2010, 54, S171-S183.
Hope K. Haefner, the Vulvodynia Guideline, Journal of Lower Genital Tract Disease, vol. 9, No. 1, 2005, 40-51.
Branko Braam, Understanding eNOS for Pharmacological Modulation . . . Current Pharmaceutical Design, 2007, 13, 1727-1740.
USP Certificate, Maritime Pine Extract LOT F0K092, The United States Pharmacopeial Convention, May 18, 2011.
K. Park, Vasculogenic female sexual dysfunction: The hemodynamic . . . International Journal of Impotence Research (1997) 9, 27-37.
Tatti et al. "Polypheon E: a new treatment for external anogenital warts", British Journal of Dermatology, vol. 162, No. 1, Jan. 1, 2010.
PCT International Search Report and Written Opinion dated Jul. 10, 2018, from PCT/US2018/019530.

(56) References Cited

OTHER PUBLICATIONS

Derogatis et al., "Validation of the Female Sexual Distress Scale-Revised for Assessing Distress in Women with Hypoactive Sexual Desire Disorder," The Journal of Sexual Medicine, 5:357-364 (2008).

Derogatis et al., "Clinically Relevant Changes in Sexual Desire, Satisfying Sexual Activity and Personal Distress as Measured by the PFSF, SAL, and PDS in Postmenopausal Women with Hypoactive Sexual Desire Disorder," The Journal of Sexual Medicine, 6:175-183 (2009).

Erekson, Elisabeth A. et al. "The VSQ: A Questionnaire to Measure Vulvovaginal Symptoms in Postmenopausal Women." Menopause (New York, N.Y.) 20.9 (2013): 973-979. PMC. Web. Mar. 17, 2016.

Rosen et al., "The Female Sexual Function Index (FSFI): A Multidimensional Self-Report Instrument for the Assessment of Female Sexual Function," Journal of Sex & Marital Therapy, 26:2, 191-208 (2000).

Symond et al., "Methods to Determine the Minimum Important Difference for a Sexual Event Diary Used by Postmenopausal Women with Hypoactive Sexual Desire Disorder," The Journal of Sexual Medicine, 4:1328-1335 (2007).

DailyMed Label: VEREGEN—sinecatechins ointment, https://dailymed.nlm.nih.gov/dailymed/drugInfo.cfm?setid=2c1cd745-79ab-487d-b759-995794cedb92, viewed Apr. 23, 2016.

Zink et al. "Green tea in dermatology—myths and facts," Journal of the German Society of Dermatology, 13(8):768-775 (2015).

Lei Xiang et al. "Status and Thoughts of Chinese Patent Medicines Seeking Approval in the US Market," Chin J Integr Med, 20(6):403-408 (2014).

Ahn et al. "Protective effects of green tea extracts (polyphenon E and EGCG) on human cervical lesions," European Journal of Cancer Prevention, 12:383-390(2003).

FDA Veregen Ointment document, 14 pages (2007).

Veregen insert, 4 pages (2006).

Veregen website, www.veregen.com, 1 page, Apr. 23, 2016.

PCT Search Report and Written Opinion dated May 31, 2016, from PCT App. No. PCT/US2016/023285.

http://www.cdc.gov/hpv/parents/whatishpv.html, Centers for Disease Control and Prevention webpage on Aug. 26, 2016.

http://dermae.com/category/160/Pycnogenol%C2%AE.html from Derma-E webpage on Aug. 26, 2016.

Merci Oi Lotion as downloaded on Dec. 6, 2019 and Jan. 10, 2020 on www.yodobashi.com/product/100000001002531206/.

Oi Lotion [Adult] merci as downloaded on Dec. 9, 2019 and Jan. 10, 2020 on www.amazon.co.jp/gp/product/B0014UGP8G/ref=sr.

Japanese Office Action for Japanese Patent Application No. 2018-500279 dated Dec. 17, 2019.

Giebink, Casey B. et al. "Managing Female Sexual Dysfunction," Women's Healthcare, Feb. 2015.

Examination Report dated Nov. 15, 2019 issued by the Indian Patent Office for application No. 201737036724.

* cited by examiner

FIG. 5A

| PATIENT QUESTIONNAIRE | 6. If you have tried or have vaginal intercourse, how would you rate the level of discomfort/pain during vaginal intercourse? |
|---|---|

PATIENT QUESTIONNAIRE

1. Please circle the area(s) below where you are experiencing discomfort or pain. You may circle as many of the listed areas that apply.

The area directly outside my vagina, at the bottom \_\_\_\_

The area directly outside my vagina on the right side\_\_\_\_

The area directly outside my vagina on the left side\_\_\_\_

The area directly outside my vagina on the top _____

Inside my vagina_____

2. Please grade the degree of discomfort or pain (from 0-4) that you are experiencing for each of the areas that you have circled above: Please place the number indicating the degree of discomfort or pain directly next to each of the area(s) that you have circled.

4=Severe   3=Significant   2=Moderate
1= Mild    0= NONE

3. How frequently are you aware of the DISCOMFORT/PAIN?
4 Always
3 Most of the Time
2 Some of the Time
1 Occasionally
0 Almost Never

4. How long have you had discomfort/pain in the area (s)?
4 I cannot remember when I did not have the discomfort/pain
3 For greater than 10 years
2 One to five years
1 less than one year
0 weeks to months

5. What activities provoke your pain?
4 I have discomfort/pain all the time it doesn't matter what I am doing
3 I have discomfort/pain only related to strenuous activities, but if I am active I have discomfort/ pain
2 I have pain/discomfort only during direct contact with the areas involved
1 I occasionally experience discomfort/pain during some activities but not frequently
0 I do not have/ no longer have any discomfort/ pain no matter what activities I am doing

6. If you have tried or have vaginal intercourse, how would you rate the level of discomfort/pain during vaginal intercourse?
4 Severe, I am unable to have vaginal intercourse or any vaginal penetration because of my discomfort/pain.
3 Significant, I have vaginal penetration but it causes me significant discomfort/ pain.
2 Moderate discomfort / pain during vaginal penetration
1 Mild discomfort during vaginal penetration
0 I do not have any discomfort/pain during vaginal penetration

7. How often are you able to become lubricated during sexual activity?
4 Never. I do not become lubricated during sexual activity
3 Rarely
2 Sometimes
1 Most of the time
0 Always

8. Do you require lubrication from sources other than your own body during sexual activity of any kind?
4 Always
3 Most of the time
2 Sometimes
1 Rarely
0 Never

9. How often are you able to experience an orgasm?
4 Never
3 Rarely
2 Sometimes
1 Most of the time
0 Always

10. How often are you able to experience an orgasm at anytime during sexual activity with a partner?
4 Never
3 Rarely
2 Sometimes
1 Most of the time
0 Always

11. Do you experience pain or discomfort after intercourse/vaginal penetration?
4 Always
3 Most of the time
2 Sometimes
1 Rarely

FIG. 5B

| | 0 Never |
|---|---|
| 12. Do you experience pain or discomfort during manual touching of the area around the outside of your vagina?<br>4 Always<br>3 Most of the time<br>2 Sometimes<br>1 Rarely<br>0 Never<br>13. What activities provoke your discomfort or pain?<br>4 sitting at rest<br>3 walking<br>2 Moderate exercise (jogging, power walking)<br>1 Intense exercise (cycling)<br>0 Intercourse<br>14. How often do you feel sexual desire/interest?<br>4 Seldom<br>3 Not often (once a month maybe)<br>2 Often (several times a week)<br>1 Occasionally ( once a week maybe less)<br>0 Frequently (daily)<br>15.Do you get aroused during sexual activity?<br>4 Never<br>3 Rarely<br>2 Sometimes<br>1 Most of the time<br>0 Always<br>16.Do you feel distressed about your sexual life?<br>4 Constantly<br>3 Frequently<br>2 Sometimes<br>1 Seldom<br>0 Never<br>17.How much is your discomfort / pain affecting your sexual life?<br>4 It has ruined the enjoyment of sexual experiences for me<br>3 It affects my sexual life very much<br>2 most of the time it impacts my sexual life<br>1 Somewhat<br>0 It has no effect on my sexual life<br>18.If you are not sexually active at the present time would you want to be if your discomfort/pain were gone?<br>4 Absolutely it is the main reason that I am not sexually active at the present time<br>3 Very much so but it is not the only reason that I am not sexually active<br>2 Probably<br>1 Maybe | 19. Describe the quality or qualities of your discomfort/pain (You may pick more than one quality)<br>4 Burning<br>3 Throbbing<br>2 knife like cutting pain<br>1 soreness<br>0 intermittent<br>Other quality not listed:<br>20.Do you experience any of the symptoms described below (please circle as many as apply to you)<br>4 Urinary incontinence (inability to control your urge to urinate)<br>3 Vaginal discharge<br>2 muscle spasms (involuntary tightening of muscles in vagina)<br>1 itching<br>0 unpleasant odor<br>21. If you have gone through menopause (because of age or surgery) how long have you been in menopause?_____Years<br><br>POST TREATMENT QUESTIONS<br><br>1. How effective was the treatment medication in relieving your discomfort or pain?<br>4 No help I still have the same level of discomfort or pain<br>3 Maybe it helped, but I am not sure<br>2 Somewhat effective, I still experience some discomfort but it is much improved<br>1 Effective , I have significantly less discomfort than before using the medication<br>0 Extremely effective, I no longer experience any discomfort or pain<br>2. Did you any problems with using the medication?<br>3. Did you experience any unpleasant side effects from the medications? Do you have any comments or suggestions that we didn't ask you but you wish to express about the treatment medication? |

FIG. 5C

| | |
|---|---|
| 0 No I am happy not being sexually active for now | |
| PATIENT GLOBAL IMPROVEMENT-INDEX (PGI-I)<br><br>"How is your condition—meaning decreased sexual desire and feeling bothered by it—today compared with when you started study medication?")<br>1. Very Much improved<br>2. Slightly improved<br>3. Improved<br>4. Unchanged<br>5. Somewhat worse<br>6. Worse<br>7. Very much worse<br><br>PATIENT BENEFIT EXPERIENCED (PBE)<br><br>"Overall, do you believe that you have experienced a meaningful benefit from the study medication?"<br><br>YES<br>NO<br><br>The PGI-I is an instrument designed to measure a patients interpretation of symptom changes following intervention. The PBE essentially asks the question: "Overall, do you believe that you have experienced a meaningful benefit from the study medication?" Additionally, the participants were asked to keep a Sexual Activity Log (SAL). The following questions were answered once a week: | 1. Indicate your most intense level of sexual desire in the past 7 days (one week)<br>No desire 0<br>Low desire 1<br>Moderate desire 2<br>Strong desire 3<br>2. How distressed have you felt about your level of sexual desire over the past week?<br>Not at all 0<br>A little bit 1<br>Moderately 2<br>Quite a bit 3<br>Extremely 4<br>3. Did you have sex in the last week<br>No 0<br>Yes 1<br>4. How many times did you have sex in the past week?<br>5. Was the sex satisfying for you?<br>No 0<br>Yes 1<br>6. Did you have an orgasm?<br>No 0<br>Yes 1 |

COMPOUNDS AND FORMS OF TREATMENT FOR FEMALE SEXUAL DISORDERS

CROSS-REFERENCE TO RELATED APPLICATIONS

This application is a continuation of U.S. application Ser. No. 15/074,984 filed Mar. 18, 2016, which claims priority to U.S. provisional application Ser. Nos.: 62/177,605 filed Mar. 19, 2015, and 62/231,345 filed Jul. 2, 2015, respectively, the contents of which are hereby incorporated by reference in their entirety.

BACKGROUND OF THE INVENTION

It is widely recognized that the human body and its associated physiology are both complex and fragile in nature. Throughout a normal human lifespan, a person will suffer from various physiological "malfunctions" mostly in the form of aging and/or disease, which reduce the quality of life, and in certain severe circumstances, may result in death. Some of these conditions are gender specific or gender selective due to the various differences in male and female anatomy and physiology. For example, uterine, ovarian and cervical cancer are female specific, whereas conditions such as prostate and testicular maladies are male specific.

One category of afflictions that specifically affect women is generally known as 'Female Sexual Disorders.' These disorders are defined in *The Diagnostic and Statistical Manual of Mental Disorders* ("DSM"), and include the following three categories: (1) Genitopelvic pain/penetration disorder; (2) Sexual interest/arousal disorder; and (3) Female orgasmic disorder. All of these afflictions are common and known to significantly reduce the quality of life for millions of women and their sexual partners.

In the most current version of DSM, (DSM-V), older terminologies, both Hypoactive Sexual Desire Disorder (HSDD) and Female Arousal Disorder were merged into a single category of female sexual disorder now called Sexual Interest/Arousal Disorder (SIAD). Similarly, the formerly separate dyspareunia and vaginismus disorders are now collectively called Genitopelvic Pain/Penetration Disorder (GPPD). The terminology Female Orgasmic Disorder (FOD) remains unchanged.

GPPD is an underreported condition and can occur at any time in a woman's life cycle. 50% of postmenopausal women suffer from a degree of genital pain/penetration disorder, and 15% of all women will experience vestibulodynia, or provoked vulvar pain, at some point in their lifetime. The prevalence of sexual interest/arousal disorder (SIAD) varies, but studies indicate a range from about 26.7% of premenopausal women to about 52.4% of naturally post-menopausal women. Lastly, 4-10% of women do not have orgasms and up to 26% of women report having at least some difficulty with having an orgasm.

The DSM-V defines genitopelvic pain/penetration disorder, (GPPD) as difficulty in vaginal penetration, marked vulvovaginal or pelvic pain during penetration, or attempt at penetration (dyspareunia), fear or anxiety about pain in anticipation of, during, or after penetration, and tightening or tensing of pelvic floor muscles during attempted penetration (vaginismus).

For many women, however, pain may occur outside the context of penetration or sexual intercourse. For example, pain or discomfort may occur during any manipulation of their external genitalia (a condition known as vulvodynia). Such pain or discomfort may be due to Vulvovaginal atrophy (VVA), including thinning of the vulvovaginal epithelium and a lack of lubrication and/or may be characterized as vulvodynia.

Vulvar pain is also a frequently occurring problem that affects both pre and post-menopausal women. Generally speaking, vulvodynia may present as more diffuse, constant vulvar pain, exhibiting a general sensation of burning or rawness in affected areas. Localized vulvodynia also known as vestibulodynia is pain around the opening of the vagina, the vulvar vestibule, most commonly found around the posterior hymenal ring between 4 and 8 o'clock, a region sometimes referred to by medical practitioners as the "posterior forchette." This is the most common cause of vulvar pain and the leading cause of dyspareunia in women under the age of 50.

This condition may manifest itself as primary vestibulodynia (i.e. pain with first attempted tampon and/or intercourse) or secondary vestibulodynia (i.e. development of vulvar pain following previously painless tampon use and/or intercourse). Conservative estimates indicate that at least 16% of women in the United States (~14 million women) have experienced some form of chronic vulvar pain. This pain and discomfort seriously impacts and degrades the quality of life. Women suffering from this condition are in need of a clinically-proven, effective treatment, as they regularly self-treat symptoms, wasting both time and money on ineffective treatments. Vulvologists from around the world, including The International Society for the Study of Vulvovaginal Disease, and practitioners from multiple professions including: medicine, psychology, physical therapy and nursing have been unable to find an effective treatment for vestibulodynia and/or chronic vulvar pain, i.e., vulvodynia. To date, there has been no effective treatment for this life-altering vulvar pain.

Genitopelvic pain in general tends to be underdiagnosed because many women are either not asked about it in connection with regular medical exams or are uncomfortable discussing it with their healthcare professional. Furthermore, genitopelvic pain/penetration disorder (GPPD) frequently becomes the cause (or a significant contributing factor) in the manifestation of sexual interest/arousal disorder (SIAD) because the anticipation of pain during sexual encounters may, over time, form a negative cognitive response that inhibits sexual interest, desire and/or arousal.

One cause of genital pain/penetration disorder (GPPD) is Vulvovaginal atrophy (VVA). Symptoms may include difficulty or inability to allow penetration, painful intercourse (dyspareunia), irritation, soreness, pain of the external genitalia, specifically of the vulva (vulvodynia), and dryness or decrease in lubrication from loss of mucous secretion. These symptoms exert a negative impact on the quality of life of up to 50% of all postmenopausal women.

Clinical diagnostic indicators of VVA include elevation of vaginal pH and a decrease in the vaginal maturation index. The low glycogen content of the thinned epithelium leads to a reduction in lactic acid production by lactobacilli bacteria, thereby increasing vaginal pH. A vaginal pH of greater than 5, in the absence of other causes, such as infection or semen from recent intercourse, is typically considered an indicator of vaginal atrophy due to lack of estrogen.

Maturation index is a term used to indicate the percentage of vaginal cell types as determined from a cytological exam of surface cells from the upper one third of the vagina. It is typically expressed as percentages of each of three cell types (i.e., parabasal, intermediate and superficial cells) found on a wet prep exam. Premenopausal women with adequate estrogen levels have a maturation index of 40% to 70% intermediate cells, 30% to 60% superficial cells, and substantially no parabasal cells (<1%). In vaginal atrophy, there is an increase in the parabasal cell population and a corresponding decrease in superficial cells, evidence of the thinning of the vaginal epithelium.

Currently, there are three types of treatments available to address the symptoms of Vulvovaginal Atrophy: 1) the topical or systemic use of exogenous estrogens, 2) The systemic use of a selective estrogen receptor modulator ("SERM") and, 3) the topical use of external lubricants or moisturizers.

The lack of estrogen is believed to be responsible for some VVA symptoms in women. This estrogen deficiency may be due to age-related menopause, or iatrogenically induced menopause which is more likely the cause of estrogen deficiency in younger, pre-menopausal, women who are estrogen deficient. However, it is important to note that genital pain, involving both dyspareunia and vulvodynia, do occur in pre-menopausal women and/or in other women having essentially normal estrogen levels. Thus, not all genital pain/penetration disorders can be adequately addressed with exogenous estrogens.

Various forms of estrogens are currently available to treat women with VVA associated genital pain/penetration disorder. They include oral estrogens with or without progestins, topical estrogens as creams, suppositories or solid hormone releasing rings (Estring). Bioidentical estrogens are 17 beta-estradiol, estrone, and estriol. Sources of estrogen maybe synthetic, animal source, (Premarin), or plant based extracted from soy or yams. Regardless of the source, however, such compounds are all still estrogenic in their inherent effects, both beneficial and adverse, on estrogen sensitive target tissues.

As a result, many women either do not want or are unable to use oral or topical estrogens, which is the current standard therapy prescribed for treating symptoms of VVA. Despite being topical, estrogens applied locally to the vagina undesirably can and do cause statistically higher levels of plasma estradiol. There are significant risks to the use of both oral and topical estrogens in post-menopausal women with or without the adjunctive use of a progestin. The Women's Health Initiative (WHI) determined the following risks to be associated with estrogen use: 1) An increased risk of endometrial cancer in a woman with a uterus who uses unopposed estrogens; 2) An increased risk of stroke and deep venous thrombosis ("DVT") in post-menopausal women using unopposed estrogens; 3) An increased risk of probable dementia in post-menopausal women using unopposed estrogens.

Further, a WHI study reported that women taking estrogen plus progestin had an increased risks of deep venous thrombosis (DVT), pulmonary embolism (PE), stroke and myocardial infarction (MI) in postmenopausal women. Additionally, an estrogen plus progestin ancillary study of the WHI reported an increased risk of developing probable dementia in postmenopausal women. The WHI estrogen plus progestin sub-study further demonstrated an increased risk of invasive breast cancer. Presently, there are no known safety studies to support the use of oral or topical vaginal estrogen in breast cancer survivors, and any estrogen use by breast cancer survivors is considered to be contraindicated by many health-care professionals.

Even while taking systemic (oral) estrogen, 10%-20% of women still suffer from certain residual VVA symptoms. Breast cancer treatment has been linked to an increase in the prevalence of VVA because the surgical, endocrine, and chemotherapeutic agents used in its treatment can cause or exacerbate VVA. As mentioned above, the use of locally applied estrogen treatment for this group of women remains controversial, and, at best, is only marginally effective.

Other currently available treatment options include the use of selective estrogen receptor modulators (SERMs), such Ospemifene (OSPHENA®), an FDA approved oral medication for moderate to severe dyspareunia (GPPD) associated with VVA due to menopause. Such SERMs act as a hormone by binding to the estrogen receptors ERα and ERβ, but bind more selectively to certain target organs such as the vagina, and thus produce less systemic estrogenic side effects compared to more non selective oral estrogens. Ospemifene, however, exerts a strong, nearly full estrogen agonist effect in the vaginal epithelium as evidenced by improvement of the vaginal maturation index and decreased vaginal pH. It is an oral medication with both systemic and local estrogenic effects that has to be taken indefinitely to maintain its therapeutic effects. Oral Ospemifene carries the risk of increased cardiovascular events such as deep venous thrombosis, stroke, myocardial infarction, thickening of the endometrium, endometrial polyps, breast tenderness, and breast lumps.

Finally, treatment options for VVA include the use of vaginal moisturizers and lubricants to provide temporary relief from vaginal dryness and dyspareunia by reducing friction. Such compounds, however, do nothing to restore the normal anatomy or function of the female genitalia; thus, they have no long-term therapeutic effects. These exogenous topically applied intravaginal therapeutics can be messy as they will leak out of the vagina when a woman is in the upright position, and are not produced by a woman's body in response to normal physiological responses to sexual stimulation. Vaginal estrogen therapy has proven more effective for VVA than all forms of non-hormonal therapy.

Another contributing cause of genital pain/penetration disorder (GPPD) is known as vestibulodynia, vulvodynia and/or vestibulitis. This affliction may be seen in up to 15% of all premenopausal women sometime in their lifetime. It is also a very common affliction of postmenopausal women unrelated to VVA.

Female vestibulodynia may be generally described as a disorder of unknown etiology where there is localized provoked vulvar pain upon penetration of the vagina. There is also tenderness to touch around the vaginal opening (vestibule) during normal self or partner's manual sexual contact or during a health professional's physical examination. The entire area around the vaginal introitus (vulvodynia) can be affected but the experienced discomfort or pain is most commonly pronounced in the localized area of the posterior forchette (vestibulodynia). The affected tissue in the vestibule has increased nerve endings and signs of inflammation and is typically painful. It occurs in women of all ages. It is estimated that approximately 15% of women (about 1 in 7) will experience this type of vulvar pain sometime in their lifetime. Vestibulodynia may lead to dyspareunia or painful intercourse and thus interfere with sexual function by causing pain in genitalia. Vestibulodynia is a challenging disorder and to date there is no definitive treatment for this condition despite a range of treatments, which include: oral tricyclics, neuromodulators (i.e., gabapentin), topical anesthetics, botulinum injections, intralesional corticosteroid injections, biofeedback, sexual therapy, psychotherapy, physical therapy, and surgery as a last resort in an attempt to remove the painful tissue. Women who have vestibulodynia often simultaneously suffer from sexual interest/arousal disorder (SIAD) and female orgasmic disorder (FOD) directly because of experiencing vestibulodynia, or provoked vulvar pain.

The two other disorders of female sexual dysfunction are: sexual interest/arousal disorder (SIAD) and female orgasmic disorder (FOD).

Sexual Interest/Arousal Disorder ("SIAD") as specified in the DSM refers to "the persistent or recurrent inability to attain or to maintain sufficient sexual excitement, which causes personal distress." In addition to absent or decreased sexual interest, including erotic thoughts or fantasies, there are four criteria that are taken into account to determine whether a woman suffers from SIAD. A woman has SIAD if she experiences personal distress caused by a decrease or lack of at least three of the following four criteria: 1) initiation of sexual activity or responsiveness to a partner's attempts to initiate it, 2) excitement and pleasure, 3) response to sexual cues, and 4) sensations during sexual activity, whether genital or non-genital. Again, three of the foregoing criteria are required for diagnosis. It may be expressed generally as lack of subjective excitement or lack of genital (lubrication/swelling) or other somatic responses.

The prevalence of Sexual Interest Arousal Disorder (SIAD), including low sexual desire, may range from about 26.7% of premenopausal women to 52.4% of naturally post-menopausal women. The disorder had no FDA-approved treatments (until August 2015 when Flibanserin, Addyi, was approved), and the FDA has recognized the condition as an area of unmet medical need.

Female orgasmic disorder, (FOD) as defined in the DSM, is the absence (anorgasmia), infrequency or delay of orgasm, and/or reduced intensity of said orgasm. Such orgasmic dysfunction may also occur when a woman has difficulty reaching orgasm, even when sexually aroused with sufficient sexual stimulation. Many women have difficulty reaching orgasm with a partner, or during masturbation, even after ample sexual stimulation. Female Orgasmic Disorder (FOD) affects approximately one in three women.

It can be difficult to determine the particular underlying cause of Female Orgasmic Disorder (FOD). Women may have difficulty reaching orgasm due to one or more physical, emotional, and/or psychological factors. Contributing factors include: older age, medical conditions, such as diabetes, a history of gynecological surgeries, such as a hysterectomy, the use of certain medications, particularly selective serotonin reuptake inhibitors (SSRIs), mental health conditions, such as depression or anxiety, stress, societal negative stereotypes of women's sexuality, lack of adequate or effective sexual stimulation, etc. Sometimes, a combination of these factors can make achieving an orgasm difficult or not possible.

The inability to orgasm can lead to distress, which may make it even more difficult to achieve orgasm in the future. The main symptom of orgasmic disorder is the inability to achieve sexual climax. Women with female orgasmic disorder (FOD) may have difficulty achieving orgasm during either sexual intercourse or during masturbation.

For many women, having unsatisfying orgasms, less intense orgasms, or taking longer than desirable to reach climax are common symptoms of FOD that lead to emotional distress.

The initial goal of therapy for female orgasmic disorder is to enable the patient to reach an orgasm as desired under any circumstance. Underlying medical etiologies must first be considered including antidepressant-induced anorgasmia, anorgasmia secondary to substance abuse, and underlying neurological disorders.

Evidence about the effectiveness of psychological therapies in successfully treating FOD is inconclusive. Testosterone in combination with estrogen has been tried, but to date no pharmacologic agents have proved to demonstrate long-term beneficial effects on orgasmic function in women with FOD, beyond a placebo effect. A Canadian company is working on a low-dose nasal testosterone gel treatment for female orgasmic disorder, FOD.

However, at present, no medication has been specifically approved by the US Food and Drug Administration (FDA) for the treatment of FOD. In addition, very little information is available about pharmacotherapy specifically targeting disorders of orgasm in women. The significant inherent risks of oral or topical hormonal therapy remain a concern.

Finally, over-the-counter (OTC) products (Zestra®) and nutritional supplements are marketed, but are ineffective in treating women with FOD. Thus, there is currently no safe or effective treatment for female orgasmic disorder (FOD) that enables an orgasm or enhances the intensity of said orgasm. Therefore, for the treatment of female orgasmic disorder (FOD), it is desirable to provide a therapeutic compound and associated treatment that is easy for the patient to use (e.g., a medication that can be applied to the affected area by the patient themselves) that shows significant improvement in orgasmic ease and intensity in a relatively short period of use and having no significant side-effects.

As discussed above, problem of SIAD encountered by many women reduces quality of life manifested as low female libido or sexual desire, and decreased or absent sexual arousal. In the past, treatments for low female libido have had little success. Some physicians have prescribed various forms of off-label testosterone preparations to increase libido with limited results. Testosterone, however, is not approved by the FDA for treating libido problems in women. Long-term safety data on testosterone therapy for postmenopausal women who have a history of breast or uterine cancer, or who have cardiovascular or liver disease, is lacking, and is being studied. Available data suggests there may be an increased risk of heart attacks, stroke, hair loss on scalp, hair growth on face, acne, heart disease, clitoralmegaly, risk of breast or uterine cancer through conversion of testosterone to estrogen, blood clots, deepening of voice, and fetal abnormalities (in pre-menopausal women).

Currently, there is no treatment for female SIAD. Thus, it desirable to provide a therapeutic compound and associated treatment that is easy for patients to use, that shows significant results in a relatively short period of time, and has no significant side-effects.

One attempt to create a safe and effective treatment for low female libido resulted in the development of the compound Flibanserin, by Sprout Pharmaceuticals, known by the tradename ADDYI, or more colloquially "The Pink Pill."

Flibanserin, (BIMT 17 BS; 2H-benzimidazol-2-one, 1,3-dihydro-1-[2-[4-[3(tri-fluoromethyl) phenyl]-1-piperazinyl] ethyl]) is a non-hormonal, centrally acting molecule that acts as an agonist at postsynaptic 5-HT1A receptors and as an antagonist at 5-HT2A receptors.

Approved by the FDA in August 2015, Flibanserin is the first and only drug indicated for pre-menopausal women for SIAD related disorders (formerly termed hypoactive sexual desire disorder). During FDA evaluation, Flibanserin, was twice rejected because according to FDA reviewers: "Flibanserin has a challenging benefit/risk assessment." This is due to its relative lack of efficacy for the intended indication as well as the prevalence of certain undesirable side effects. For example, from a median baseline of about 2-3 satisfying sexual events ("SSEs") per month, Flibanserin resulted in a median placebo-corrected increase of only about 0.5-1.0 SSEs per month over a six month period. Moreover, this marginal benefit was seen in only 18% of women taking 100 mg daily of the systemic drug for a minimum of 28 days.

During trials, it was observed that the risks of sedation or hypotension-related adverse events are substantially higher with Flibanserin vs placebo (28.6% Flibanserin vs 9.4% placebo). Flibanserin acts on the central nervous system and must be taken continuously and indefinitely. Side effects of Flibanserin are significant and include hypotension, syncope and somnolence. The risk of such side effects is amplified by drug interactions with CYP3A4 inhibitors such as oral contraceptives or Fluconazole and with concomitant alcohol intake. The FDA concluded that the clinically significant pharmacodynamic interaction between Flibanserin and alcohol is challenging to mitigate, particularly because Flibanserin requires daily use and alcohol consumption, including excessive drinking, is not uncommon in many cultures and further common for those engaging in sexual activity. The combination of ethanol and Flibanserin resulted in concerning cases of hypotension and pre-syncope/syncope. In addition, Flibanserin trials were limited to generally healthy women who were not taking additional medication such as benzodiazepines, sleep aids, narcotics, or other medicines. As with many drug trials, Flibanserin trials were of short duration relative to the potential length of time that Flibanserin could be indicated. Further, it is noteworthy that Flibanserin demonstrated no therapeutic effect at all on Genitopelvic pain/penetration disorders (GPPD) including vestibulodynia and dyspareunia or on Female Orgasmic Disorder (FOD).

Thus, in view of the foregoing, there is currently a lack of safe efficacious treatments for Female Sexual Disorders including genitopelvic pain/penetration disorder (GPPD), sexual interest/arousal disorder (SIAD), and female orgasmic disorder (FOD).

SUMMARY OF THE INVENTION

The invention provides safe and efficacious treatments for Female Sexual Disorders, genitopelvic pain/penetration disorders; vulvovaginal atrophy, vestibulodynia, dyspareunia, sexual interest/arousal disorder, female orgasmic disorder, and low female libido.

The catechin compounds and treatment methods described herein show significant efficacy for treatment of genitopelvic pain disorder (GPPD), sexual interest arousal disorder (SIAD) and female orgasmic disorders (FOD). They are efficacious in treating genitopelvic pain disorder (GPPD) due to VVA without estrogenic side effects as demonstrated by lack of change in pH or vaginal maturation index. The catechin compounds of the present invention are further efficacious in reducing vestibulodynia or provoked genital pain and dyspareunia (GPPD), increasing vaginal lubrication as well as improving sexual interest/arousal disorder (SIAD) by increasing sexual interest and arousal. Additional benefits of the present invention include increasing the intensity and frequency of a woman's orgasm, and therefore is efficacious in treating female orgasmic disorder (FOD). This is a surprising result because prior art 15% catechin formulations used to treat human papilloma virus (HPV) infections are associated with significant vulvovaginal irritation, discomfort or pain. In contrast, the methods and compositions of the inventions described herein have substantially the opposite effect. They soothe the vulvovaginal area and relieve the symptoms of GPPD, SIAD, FOD, and VVA.

Thus, the invention provides a method for treating a female sexual disorder, comprising administering a pharmaceutical composition to an individual's vulvovaginal area, wherein said pharmaceutical composition comprises a catechin. In some embodiments, said female sexual disorder is sexual interest/arousal disorder (SIAD), genital pelvic pain disorder (GPPD), or female orgasmic disorder (FOD).

In other embodiments of the methods described herein, said catechin is at a concentration of between about 1% and 10% weight per weight of total composition (w/w). In a preferred embodiment, said catechin concentration is between about 2.5% and 10% by weight. In a more preferred embodiment, said catechin concentration is between about 1% and 7.5%. In a most preferred embodiment, said catechin concentration is about 5%.

In another embodiment of the methods described herein, said catechin is a tea catechin. In a more preferred embodiment, said catechin is a green tea catechin. In a most preferred embodiment, said catechin is epigallocatechin.

In some embodiments of the methods described herein, said catechin is applied to a vulva, a vaginal introitus or a vagina. In other embodiments, said pharmaceutical composition is an ointment, a lotion, an emulsion, an aqueous solution, or a non-aqueous solution.

In some embodiments of the inventions described herein, said pharmaceutical composition further comprises a selective estrogen receptor modulator (SERM). In a preferred embodiment, said SERM is ospemifene. In other embodiments, said pharmaceutical composition further comprises estrogen. In other embodiments, said pharmaceutical compositions further comprise a combination of both a SERM and an estrogen hormone.

The invention provides a pharmaceutical composition, comprising a catechin at a concentration of between about 1% and 10% weight per weight of total composition (w/w) and a pharmaceutically acceptable carrier. In a preferred embodiment, said catechin concentration is between about 2.5% and 10% by weight. In a more preferred embodiment, said catechin concentration is between about 1% and 7.5%. In a most preferred embodiment, said catechin concentration is about 5%.

In other embodiments, the pharmaceutical compositions described herein comprise a tea catechin. In a preferred embodiment, said catechin is a green tea catechin. In a more preferred embodiment, said catechin is epigallocatechin.

In some embodiments of the invention, the pharmaceutical compositions described herein are formulated for application to a vulva, a vaginal introitus or a vagina. In other embodiments, the pharmaceutical compositions described herein are formulated as an ointment, an emulsion, an aqueous solution, or a non-aqueous solution.

In some embodiments, the pharmaceutical compositions described herein further comprise a selective estrogen receptor modulator (SERM). In a preferred embodiment, said SERM is ospemifene. In other embodiments, said pharmaceutical composition further comprises estrogen. In other embodiments, said pharmaceutical compositions further comprise a combination of both a SERM and an estrogen hormone.

In some embodiments, the pharmaceutical compositions of the invention further comprise an extract or essential oil from a source selected from the group consisting of ascorbic acid, vitamin E, omega 3, salt water, menthol, agar essential oil, agar extract, ajwain, aloe vera, amyris, angelica root, anise, balsam, basil, bay rum, bergamot, black pepper, buchu, butterbur, cajeput, cannabis flower, caraway, cardamom seed, carrot seed, cedarwood, Cedarleaf, chamomile, cinnamon, cistus, citrus vulgaris, citronella, clary sage, clove leaf, coriander, costmary, cranberry seed, cumin/black seed, cypress, davana, dill, eucalyptus, fennel seed, fenugreek, frankincense, galbanum, geranium, ginger, grapefruit, grape seed (e.g. Vitis vinifera), henna, jasmine, juniper berry, lavender, lemon, lemongrass, lime, litsea cubeba, lobelia/neem, melissa (Lemon balm), mentha arvensis/Mint, mugwort, mustard, myrrh, neroli, nutmeg, orange, oregano, orris, parsley, patchouli, perilla, pennyroyal, peppermint, pine, rose, rosehip, rosemary, rosewood, sage, sandalwood, sassafras, savory, schisandra, spearmint, star anise, tarragon, tea tree, thyme, vetiver, and yarrow ylang-ylang. In a preferred embodiment, the extract is from peppermint.

DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 5A is a patient questionnaire.
FIG. 5B is a patient questionnaire.
FIG. 5C is a patient questionnaire.

DETAILED DESCRIPTION OF THE INVENTIONS

Figure 1A:
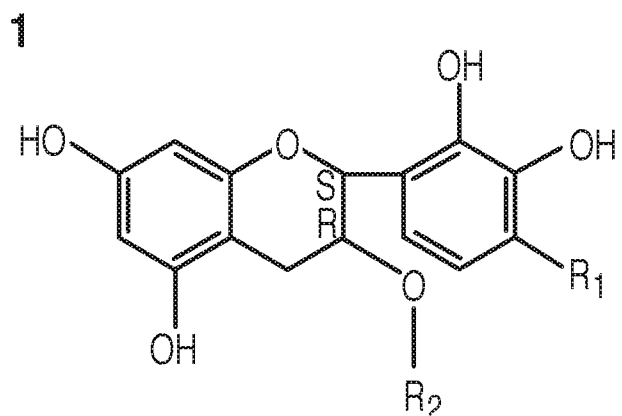
FIG. 1A is a generalized chemical structure (1) of a catechin in accordance with one embodiment of the present invention. Functional groups can be added at R1 and R2. "S" and "R" refer to the stereochemistry at the indicated position.

The invention provides, for the first time, a method of treating female sexual disorders with green tea catechins. Previously, topically-applied green tea catechins were used to treat human papilloma-based (HPV) neoplasms. These topical formulations, however, caused significant vulvovaginal discomfort or pain at the catechin concentrations used. Thus, it was surprisingly found that lower concentrations of catechins had the opposite effect, namely, soothing vaginal discomfort, pain, increasing vaginal lubrication, increasing sexual interest and desire, and increasing the frequency and intensity of orgasms. Thus, the result was an amelioration of a variety of female sexual disorders. This is a significant public health benefit because the disclosed inventions may be used, optionally, without any female hormones or systemic-based treatments.

In accordance with one embodiment of the invention, effective primary catechin treatment preparations may start at about 1% and go up to about 10% catechin measured by weight of active ingredient per weight of total formulation (w/w). The formulations are, for example, ointments, lotions, emulsions, water soluble solutions, and water-insoluble solutions. Further exemplary compositions include liposomes, microparticles, and nanoparticles. Secondary treatment preparations for maintenance of therapeutic effect may be about 1% catechin by weight water soluble extract in various deployment preparations or, alternatively, may be increased up to about 12-20% catechin by weight preparation, depending on the individual's therapeutic response and acclimation to treatment over time. The catechin preparations may be directly applied to the vulvar skin and the vaginal introitus at regular intervals in a manner to cover affected areas with a thin layer of the preparation such as an ointment. Other preparations may include spray on or other suitable topical deployment vectors. The frequency of application may start at once a day and either be increased up to about twice a day or decreased to about twice per week for women with either very sensitive skin, or for women who have achieved the desired therapeutic effect and are using it for maintenance.

Typically, preparations of 5% by weight catechin in petrolatum base spread across the affected area are sufficient for treatment. Preparations that have a concentration of more than 10% by weight catechin tend to cause irritation and cancel out the therapeutic effects of the present invention if used during initial treatment. Typically, a preparation of about 2.5%-7.5% by weight catechin is initially prescribed. Preparations with lower concentration may be used for women with sensitive skin types (e.g., 2.5%). Alternatively, the catechin percentage may be increased to about 7.5%. For most women, daily use of about 1-2 CCs (cubic centimeter) of 5% by weight catechin in petrolatum base spread across the affected area is sufficient for treatment.

The catechin preparations of the present invention are topical, well tolerated, have no significant side-effects, may be safely applied for a long period of time by the patients themselves and is notably effective in treating and alleviating the signs and symptoms of Female Sexual Disorders (SIAD, GPPD, and FOD). Furthermore, the present invention will likely be classified by the FDA as a phase 3 botanical drug according to the 2004 USA FDA CDER guidelines.

The mechanism of action of catechins according to the present inventions is not fully understood. In vitro, green tea catechins demonstrate antioxidative properties. Catechins also possess immune-stimulating effects and antiviral and anticarcinogenic properties that cause inhibition of enzymes involved in the pathogenesis of human papilloma virus. Of note, whereas catechins have anticarcinogenic properties, estrogens, the current standard of care for VVA, can promote carcinogenesis and are contraindicated in breast and uterine cancer patients.

Although, the exact mechanism of action of the present invention in not fully understood, it is known that sensations of pain interfere with sexual response. Thus, one mechanism of action for female sexual arousal and orgasmic response in accordance with an aspect of the present invention is believed to be attributable, at least in part, to a neuromodulatory effect of catechins on portions of the nervous system innervating the vulva, clitoris, vaginal introitus, labium, perineum and vagina whereby aberrant nociceptive sensory innervation is reduced so as not to interfere with the perception of pleasurable sexual sensations. Another neuromodulatory mechanism of action of catechins is believed to be attributed to a positive stimulatory effect of catechins on sensory afferents located in these same areas of female anatomy.

The mechanism of action of the catechin preparations of the present invention on VVA and vulvodynia, vestibulodynia may involve reducing the pathological proliferation of nerves (both autonomic and peripheral) of affected vaginal mucous membranes found in all three conditions. This may be shown by histopathological analysis of relevant tissues. Further, catechin preparations of the present invention (sometimes referred to herein as "GTO" or green tea ointment) may act to selectively bind to certain estrogen receptors in the female genitalia providing localized relief, but with little or no systemic side effects. This is evidenced by the lack of proliferation of vaginal epithelium in response to GTO treatment. Rather, GTO acts locally and specifically as a topical phytoestrogen on the normalization of innervation to the genital skin. This is further evidenced by the lack of alteration in the vaginal maturation index. The effect of topical GTO is localized to the external genitalia, and, particularly the vaginal introitus and vestibule where it was necessary and was sufficient for treatment being applied only to those areas.

Immuno-histochemistry analysis of vulvar skin of women with vulvodynia has shown altered density of nociceptor nerve endings and an increased number of intraepithelial free nerve endings, lowered tactile and pain thresholds, nociceptor sensitization and overall peripheral nerve hyperplasia. Provoked vulvodynia, is characterized by genital hypersensitivity and sensory hyperinnervation.

Although direct effects of estrogen withdrawal on vaginal cells are implicated in VVA, (e.g., thinning of the vaginal epithelium) estrogen withdrawal also causes autonomic and sensory nerves to proliferate, suggesting that indirect effects mediated by changes in vulvar vaginal innervation may also contribute to pain associated with VVA.

Symptoms of VVA and GPPD (vulvodynia and dyspareunia) can be caused by proliferation of autonomic and sensory nerve vulvar vaginal innervation density. Because topical estrogens are more effective than systemic estrogens in the treatment of VVA pain by causing a reduction of abnormal vulvar vaginal innervation the same or similar mechanism may explain why topical GTO's (a phytoestrogen) application to vulvar mucosa is so effective in alleviating vulvar pain and dyspareunia.

Reduction or normalization of nociceptive (or pain afferent) pathways that are localized in the area of the vaginal introitus and posterior forchette underlies the therapeutic efficacy that is well established through the application of topical estrogen. In view of these observations, the catechin preparations of the present invention are believed to be acting locally without any substantial systemic effects whatsoever as a phytoestrogen. Even when given in large systemic doses to postmenopausal women, green tea and associated catechins have substantially no effects on any systemic estrogen levels.

It is known that certain catechin-based green tea compounds may be used for the treatment condyloma acuminata or genital warts. This is used strictly to treat viral-based papilloma manifestations, such as wart populations on certain areas of the genitalia and anus. For example, see U.S. Pat. Nos. 5,795,911 and 5,968,973 to Chen et al. However, as is well known in the art, the treatment of such viral-based maladies is very different from the Female Sexual disorders described herein because the indication for use of "sinecatechins," is for the reduction of condyloma acuminata, or genital warts caused by infection with human papilloma virus. The mode of operation for wart treatment is prescribed because the water soluble extract of green tea leaves possesses antiviral, antiproliferative, and immunostimulatory activity. Therapeutic applications of the green tea water soluble extract is thought to be efficacious due to the specific inhibition of multiple HPV-induced pathways by sinecatechins that is believed to contribute to the reduction or clearance of genital warts, likely via direct antiviral and immunostimulatory effects.

Catechins are used to treat genital warts and other HPV-related conditions because of their antiviral and immunostimulatory activity. Prior to the present invention, they were not used to treat female sexual disorders. This is likely because the highly-concentrated catechin preparations described in Chen et al. are preferably in the 12%-18% range by weight. At such concentrations, the irritation they cause, together with HPV pain, masked the benefits of the inventions described herein. The known anti-viral effects of catechins were not known to have any effect on female sexual disorders as described in the present invention. The regenerative and restorative effects of the present invention are an apparent opposing effect when compared to the prior art highly-concentrated catechin preparations. Accordingly, the results and findings herein were unexpected.

Thus, the invention provides a topical formulation for the treatment of Female Sexual Disorders including genitopelvic pain/penetration disorder; sexual interest/arousal disorder; female orgasmic disorder, VVA and other vulvovaginal disorders, including but not limited to vestibulodynia. The content of catechin may be between about 2.5-7.5% by weight for initial treatment.

The prevalence of sexual interest/arousal disorder (low sexual desire) may range from about 26.7% of premenopausal women to 52.4% of naturally postmenopausal women. Between 4 and 10% of women do not have orgasms, and up to 26% of women report some difficulty with having an orgasm.

Topical GTO can increase a woman's desire, arousal, lubrication, satisfaction and orgasm (intensity and/or frequency) and her frequency of satisfying sexual events, as well as decrease her genital pain and dissatisfaction about her level of sexual desire (Item #13 in Sexual Distress Revised). Topical GTO demonstrates far greater efficacy without any serious side effects as compared to Flibanserin, marketed under the tradename, Addyi, or the "The Pink Pill". Flibanserin has marginal efficacy in only 18% of patients taking it for a minimum of 28 days. Flibanserin is a systemic drug that must be taken indefinitely with potential serious side effects of syncope, hypotension and somnolence especially if combined with alcohol.

GTO has a rapid onset of action with all demonstrated clinical changes occurring within days to weeks after regular topical application of GTO. Clinical improvement continues over the month of use and concentration of the drug may be increased as tolerated to maximize efficacy. Topical GTO has no known systemic side effects. Potential local side effects and the safety profile are well documented for GTO because of the FDA approved herbal drug Veregen, (15% GTO). Local irritation is the most common local side effect, and it is more likely to occur the higher the concentration of GTO. Clinical evidence of direct anti-inflammatory effects of the lower concentration (5%) GTO on the genital mucosa are documented in the application presented herein.

It is known that pain interferes with sexual response. Thus, the invention provides increasing female sexual interest and arousal and orgasmic response is through amelioration of genital pain. While not wishing to be bound by theory, the benefits of the invention may be, at least in part, due to a neuromodulatory effect of catechins on portions of the nervous system innervating the vulva, clitoris, vaginal introitus, labium, perineum and vagina.

One mechanism of action for female sexual arousal and orgasmic response in accordance with an aspect of the present invention is believed to be attributable, at least in part, to substantially direct neuromodulatory effects of green tea catechins on nerves innervating the female genitalia.

The innervation of the female genital tract is mediated through the somatic and the autonomic nervous systems. Green tea polyphenols and catechins, demonstrate both a positive stimulatory and negative inhibitory effects on portions of the autonomic and somatic nervous systems innervating the vulva, clitoris, vaginal introitus, labium, perineum and vagina. Polyphenols and catechins, of green tea can interact with a range of neurotransmitters and thereby effect neuronal events including modulating neurotransmission, plasticity and synaptogenesis.

As is known in the art, the therapeutic effects of pharmaceuticals on target tissues are frequently dose dependent. For virtually all drugs treatment protocols there are dosage parameters where the therapeutic benefit of the drug is manifest but where exceeding that therapeutic dosage range causes adverse, unwanted side effects, and in some cases, toxicity or exacerbation or worsening of condition for which the drug was supposed to benefit, which is generally undesirable and is avoided.

This dose dependent effect is true with respect to green tea catechins. For example, the clinical outcome of green tea catechins treatment is apparent with respect to modulation of myocardial contractility. Epigallocatechin-3-gallate (EGCG) is a major and potent representative in green tea, which has been proved to modulate myocardial contractility. EGCG at low dose conferred cardioprotection, yet at high dose increased the incidences of arrhythmia and diastolic dysfunction. Green tea at low doses was therapeutic but proved toxic at high doses.

With respect to the present invention, initial testing with 15% by weight GTO was found to be irritating and too uncomfortable and therefore was not well tolerated, especially when treating subjects with preexisting genital pain. These adverse side effects of 15% by weight GTO precluded observing any evidence both of its efficacy and observable clinically effectiveness as a treatment for female sexual disorders. In fact, the adverse clinical side effects seen with 15% GTO both obscured and/or negated the positive effects seen with the lower concentration in accordance with aspects of the present invention. This dose dependent response of GTO, along with HPV pain, explains why the higher concentration formulations of GTO were not recognized as having any beneficial effects on female sexual disorders.

The surprising therapeutic effect of 5% GTO applied to the female genitalia target tissues with a frequency from 2-3 times per week up to twice daily use, improved the female sexual response by both enhancing sexual responses and reducing genital pain. Once these therapeutic benefits of 5% GTO are manifest or if there is habituation of a positive therapeutic response, then the frequency of application and/ or the concentration of GTO may be increased.

In general, the normal female sexual response depends on the function of the peripheral autonomic nervous system and intact signaling pathways controlling the tone of genital vascular and nonvascular smooth muscle.

Autonomic adrenergic systems are active in women when they become sexually aroused and their activation facilitates female sexual arousal. Adrenaline and noradrenaline metabolite, vanillylmandelic acid, increases prior to intercourse and continues to be elevated over baseline up to 23 hours following sexual activity. In addition, ephedrine, an α- and β-adrenergic agonist, can significantly facilitate the initial stages of physiological sexual arousal in women. EGCG, action on stimulation can be attributed to its substantially direct effect on autonomic adrenergic receptors. These effects influence autonomic nerve pathways that send afferent signals up the spinal cord to the hypothalamus causing release of hormones during orgasm in addition to efferent autonomic pathways sending neural impulses to effect blood flow, lubrication, smooth muscle contraction in the female genitalia.

As noted herein, green tea catechins' effect on autonomic adrenergic receptors is dose dependent, especially during the initial stages of treatment. The present invention starting at about 5% GTO (e.g., 2.5%-7.5%) has been shown to improve sexual arousal, lubrication and female orgasmic response and decrease genital pain.

During a sexual encounter, sexual sensations from somatic sensory nerve pathways from branches of the pudendal nerve are responsible for sending somatic sexual sensations from the genitalia up the spinal cord to the cerebral cortex. Complete spinal cord injuries typically result in loss of somatic sensation and autonomic sexual inarousability of innervated body parts below level of injury, whereas incomplete injuries result in some sensation and arousability.

HPV infection is not the cause of vulvodynia as most women affected with vulvodynia and vestibulodynia have been shown not to be infected with HPV or have any evidence of HPV infection. Rather, exogenous progesterone, such as found in certain contraceptives, has been shown to be a factor in causing vulvodynia and vestibulodynia. In addition, estrogen withdrawal is a known etiology of genital pain seen in VVA. Conventional treatment for this is topical estrogen cream. This cream reduces the pain in both VVA and in some cases of vulvodynia/vestibulodynia but has no effect whatsoever on HPV. In fact, high estrogenic states such as pregnancy can increase the proliferation of HPV.

Thus, GTO's beneficial therapeutic effect on female sexual disorders is not due to GTO's effect on HPV.

The primary focus for sensual response in the human female is the clitoris. The first branch of the pudendal nerve, the dorsal nerve of the clitoris, is a purely sensory nerve without any known motor functions. The second branch of the pudendal nerve, the perineal nerve, provides sensory branches to the perineum, labia majora, labia minora and distal third (the perceptually most erogenous portion) of the vagina and also has motor effectors. The dorsal nerve (the first branch of the pudendal nerve) only carries somatosensory impulses from the clitoris. Its' only known function is that of serving as an erotic focus. The clitoris, in its entirety, has been shown to be the most erotically sensitive part of female genital anatomy. Maximum nerve density is known to be in and around the clitoris. The most intense sexual sensations in the human female come from clitoral stimulation. The anatomical site with the strongest orgasmic response requiring the least amount of stimulation necessary to obtain an orgasm involves the clitoral stimulation. The distribution of enhanced sexual sensations, experienced during the use of the present invention, correlate most closely with dorsal nerve or clitoral branch of the pudendal nerve, innervating the entire clitoris, the central external visible glans and body of the clitoris and the so called "internal" or hidden clitoral crus which bifurcate and extend alongside the right and left ischial pubic rami innervating the lateral walls of the vagina extending anteriorly to the vaginal introitus.

Of note vestibulodynia is characteristically localized to the lateral edges of the vaginal introitus. One effect of GTO is thought to be due to its therapeutic effect on reducing the pathogenic hyper innervation of this area of the vaginal vestibule also termed posterior forchette in females afflicted with VVA and or vestibulodynia/vulvodynia (i.e., excessive innervation in the "wrong" area of the genitalia). This decreases nociceptive innervation and thus sensations of pain. GTO's effect here may be due in part because of GTO's inherent property as a phytoestrogen in its selective effect on target tissues without systemic side effects of exogenous estrogen.

The first branch of the pudendal nerve, the dorsal nerve of the clitoris, is responsible for sensations in the clitoris and increased estrogen levels expand the size and sensitivity of the pudendal perineal innervation. Topical application of Green Tea Ointment, GTO, may be acting to increase the sexual sensitivity, arousal and orgasm by expanding the size and sensitivity of the pudendal nerve's innervation. Further, topical GTO, may act to selectively bind to certain estrogen receptors in the female genitalia, specifically the vaginal introitus and vestibule. This reduces abnormal hyperproliferation of nociceptive nerves and provides localized pain relief with no systemic side effects or risks inherent in either topical or systemic estrogens. GTO is a known phytoestrogen without the inherent side effects of exogenous estrogens. This is evidenced by the lack of proliferation of vaginal epithelium in response to topical GTO treatment and by the lack of alteration in the vaginal maturation index of woman using GTO. The safety of GTO use is further demonstrated by the lack of alteration in systemic estrogen levels, even with systemic, rather than topical use of Green Tea catechins. Even when given in large systemic doses to postmenopausal women, green tea and associated catechins have substantially no effects on any systemic estrogen levels. Thus, the use of GTO of the present invention is preferred in the treatment of female sexual disorders as compared to the current conventional use of exogenous estrogens in women, which had numerous well known risks.

Autonomic innervation of the female genitalia is comprised of nerve fibers from both the sympathetic and parasympathetic nervous systems. Sympathetic fibers are derived from the lower thoracic and upper lumbar spinal segments (T10-L2), and the parasympathetic nerve fibers are derived from S2-4. These autonomic fibers, both sympathetic and parasympathetic then coalesce in the pelvis and redistribute to the genital target organs (uterus, cervix, proximal ⅔'s of the vagina). Autonomic sensory afferent fibers are believed to follow the same course starting at the genital target organs coalescing in the pelvis and returning to the spinal cord segments.

Female sexual responsivity is a result of sensory input through the peripheral nerves of the somatic and autonomic nervous systems, as well as through cranial nerves and psychogenic stimulation. How and where the afferent information is processed within the spinal cord and brain is not fully known.

Reflex lubrication where a tactile stimuli from the genitalia travels up the spinal cord to and reflexively connect to spinal efferent pathways travels back down the spinal cord to the nerves innervating the vaginal vasculature can occur if an injury is above T9 and not involving T10 to T12 where presumably the reflexive autonomic lubrication center in the spinal cord is located.

GTO and Orgasmic response: The afferent sensory sensations are conducted upwards through the spinal cord where there is a pathway for a spinal reflexive orgasmic response as evidenced by the ability of some women with spinal cord injuries to experience orgasms. However, even with complete spinal cord injuries, some women can experience an orgasm, indicating other nerve pathways that bypass the spinal cord. Impulses ultimately reaching the cerebral cortex, in particular the temporal lobe and the posterior pituitary via the hypothalamus, effect perception of pleasure and among other efferent response, posterior pituitary release of oxytocin and prolactin during enhanced female orgasmic experience. There is a measurable significant increase in blood flow in the posterior pituitary during a human female's orgasm with its release of oxytocin and prolactin. Men unlike women do not demonstrate such large releases of oxytocin and prolactin during orgasm. It is believed that the topical application of GTO in accordance with an aspect of the present invention increases sensory neuronal innervation in and around the clitoris, and, in its entirety (glans, body and crus), is enhancing the pituitary's release of oxytocin and prolactin and the woman's perception of pleasure in her cerebral cortex by increasing the afferent signaling traveling up the spinal cord.

GTO and GPPD: GTO normalizes the nervous innervation by increasing sensory nerve innervation of the dorsal branch of the pudendal nerve in and around the clitoris while GTO acts to decrease the abnormally high nerve density around the vaginal vestibule. By these effects GTO increases positive sexual sensory sensations and resultant orgasmic responses but decreases genital pain in and around the vaginal introitus and vestibule as seen in VVA and vulvodynia and vestibulodynia.

Thus, GTO increases neural innervation of the dorsal nerve of the clitoris and thereby stimulating or augmenting sexual sensations and arousal. It also decreases the aberrant hyperinneration of both autonomic and somatic sensory fibers in and around the vaginal introitus, specifically posterior forchette. This decreases genital pain.

Sexual response includes desire, arousal, lubrication and orgasm. It is known that, if perceived as unpleasant or toxic, sensations of pain can interfere with a woman's sexual response. Genital pelvic pain disorder in VVA and vulvodynia, vestibulodynia is characterized by genital hypersensitivity and sensory hyperinnervation with unmyelinated sensory nociceptor neurons. Although direct effects of estrogen withdrawal on vaginal cells is implicated in VVA, (e.g., thinning of the vaginal epithelium) estrogen withdrawal also causes both autonomic and somatic sensory nerves to proliferate, suggesting that indirect effects mediated by changes in vulvar vaginal innervation may be a major contributor to pain associated with VVA. This has been shown by histopathological analysis of relevant tissues. Topical application of estradiol is a well-documented and effective therapeutic for pain associated with VVA.

Exogenous progesterone use, in contraceptives, in premenopausal women, may be one etiology of vulvar hyperinnervation in vestibulodynia and or vulvodynia. Progesterone can induce both autonomic and somatic sensory nerves to proliferate. Oral progesterones can increase the risk of developing vestibulodynia by four to ninefold. Topical estradiol has been shown to reduce the sensory hyperinnervation and vulvar pain associated with vestibulodynia and vulvodynia.

The mechanism of action of the catechin preparations of the present invention on VVA and vulvodynia, vestibulodynia may involve reducing the pathological proliferation of sensory nerves, hyperinnervation of affected vulvovaginal mucous membranes found in in all three conditions associated with female Genital Pelvic Pain Disorder (VVA, vulvodynia, vestibulodynia). Immuno-histochemistry analysis of vulvar skin of women with VVA and vulvodynia have shown increased density of nociceptor nerve endings and an increased number of intraepithelial free nerve endings, lowered tactile and pain thresholds, nociceptor sensitization and overall peripheral nerve hyperplasia. This sensory nociceptor axon proliferation may contribute to symptoms of pain, burning and itching associated with VVA and some forms of vulvodynia.

GTO, in accordance with aspects of the present invention is thought to be acting as a topical phytoestrogen on the normalization of innervation to the genital skin. The effect of topical GTO is localized to the external genitalia, and, particularly the vaginal introitus and vestibule where it is both necessary and sufficient for alleviation of pain associated with VVA, vulvodynia and vestibulodynia.

Symptoms of VVA and GPPD (vulvodynia, vestibulodynia and dyspareunia) can be caused by proliferation of autonomic and sensory nerve vulvar vaginal innervation density. It is well documented that topical estrogens are more effective than systemic estrogens in alleviating the pain in VVA and vulvodynia/vestibulodynia by reducing and therefore normalizing of abnormal vulvar vaginal hyper innervation. Reduction or normalization of nociceptive (or pain afferent) pathways that are localized in the area of the vaginal introitus and posterior forchette, vaginal introitus in VVA and vulvodynia, vestibulodynia is the most likely mechanism for the therapeutic efficacy of the application of topical estrogens. It is hypothesized that the same or similar mechanism is why topical GTO's (a phytoestrogen) application to vulvar mucosa and vaginal introitus is so effective in alleviating vulvar pain and dyspareunia in both VVA and vulvodynia/vestibulodynia. In view of these observations, the GTO, catechin preparations of the present invention are believed to be acting locally without any known systemic effects whatsoever (as a phytoestrogen).

Antiandrogens exert estrogenic effects on target tissue by blocking the effect of androgens at the cellular level. Green tea catechins estrogenic-like effects may be attributed to epigailocatechin by inhibiting 5-alpha reductase. This reduces the conversion of testosterone to the more potent androgen dihydrotestosterone.

Another ancillary mode of action of the present invention is on mucous membranes, in connection with its antioxidant effect which might help reduce inflammation and irritation that can, but not necessarily, be a factor in VVA and vulvodynia.

GTO and lubrication: Lubrication is controlled by both somatic and autonomic neural impulses that travel through the spinal cord. Autonomic fibers send efferent impulses back to genitalia smooth muscle with effects on both vasodilation and therefore lubrication. There is absence of lubrication in women either reflex or psychogenic when the spinal cord is severed between T10 and T12. Psychogenic lubrication, or lubrication in response to non-tactile stimuli is possible if the spinal cord is severed below T12, presumably from neural pathways traveling from cerebral cortex down to spinal centers responsible for autonomic efferent neural pathways innervating smooth muscle and nerves of the vagina. Reflex lubrication where a tactile stimuli from the genitalia travels up the spinal cord to and reflexively connect to spinal efferent pathways travels back down the spinal cord to the nerves innervating the vaginal vasculature can occur if an injury is above T9 and not involving T10 to T12 where presumably the reflexive autonomic lubrication center in the spinal cord is located.

Some aspects of vaginal dysfunction during menopause may be attributable to changes in innervation. Increased sympathetic innervation may augment vasoconstriction and promote vaginal dryness. GTO acting as a phytoestrogen, decreasing aberrant hyperinnervation may be one mechanism whereby GTO increases vaginal lubrication. Another mechanism of the action of GTO catechins on vaginal lubrication would be its direct effect on neurotransmitters on vascular smooth muscle.

The normal female sexual response depends on the function of the peripheral autonomic nervous system and intact signaling pathways controlling the tone of genital vascular and nonvascular smooth muscle.

The first measurable sign of sexual arousal is an increase in vaginal blood flow. This creates the engorged condition, that saturates the fluid resabsorptive capacity of the vaginal epithelium. This results in increase in vaginal fluid, i.e. lubrication which enables less friction during coitus.

Genital motor responses to sexual stimulation including vaginal lubrication is mediated by autonomic vasoactive neurotransmitters including, vasoactive intestinal peptide (VIP) and Nitric oxide synthetases.

The mechanisms underlying vaginal lubrication appear to be mediated by several vasoactive neurotransmitters especially vasoactive intestinal peptide (VIP). VIP injection into or topical application to the vaginal wall increases vaginal blood flow and induces vaginal fluid production.

Green tea catechins interact with a range of neurotransmitters and other signaling molecules. Nitric Oxide cyclic guanosine monophosphate pathway is involved in the physiological mechanism of female genital arousal. Endothelial Nitric oxide synthases (NOS) and VIP vasoactive intestinal peptides are co-localized in the human vagina. Nitric Oxide synthases are located on the vaginal vessels in close proximity to vasoactive intestinal peptides (VIP) on the vaginal nerve fibers. They are both directly involved in effecting vaginal blood flow and thus lubrication. Disturbances in these pathways are thought to contribute to the pathophysiology of sexual dysfunction. Nitric oxide relaxes genital vascular and nonvascular smooth muscle which plays a pivotal role in mediating the normal sexual response to visual and/or tactile erotic stimulation. Insufficient bioavailability of Nitric oxide and/or vasoactive intestinal peptide decreases vasodilation which decreases vaginal lubrication. Catechin isolated from green tea has been shown to substantially directly effect the level of NO in endothelial cells. It is by this effect of green tea catechin on the level of Nitric Oxide in endothelial cells that the use of GTO in accordance with aspects of the present invention increase lubrication is efficacious.

One of green tea's catechins, EGCG, affects adrenergic receptors. Activation of epithelial beta adrenergic receptor pathways facilitates vaginal lubrication during sexual arousal. Green tea's action on facilitating vaginal lubrication may be attributed to its direct effect on beta adrenergic receptor pathways. Activation of epithelial beta adrenergic receptors facilitates vaginal lubrication during sexual arousal by stimulating vaginal epithelial Cl(−) secretion in a cAMP-dependent pathway. Adrenergic alpha-receptors (AR) are an important regulator of genital physiological responses involved in mediating vascular and nonvascular smooth muscle contractility. The concentration of EGCG effects which of the adrenergic receptors (alpha or beta) will be activated. At higher concentration it is shown that EGCG can activate the β2Areceptor. Topical application of GTO directly to genital mucosa would enable higher concentrations of EGCG and facilitate enhancement of vaginal lubrication.

Figure 1B:
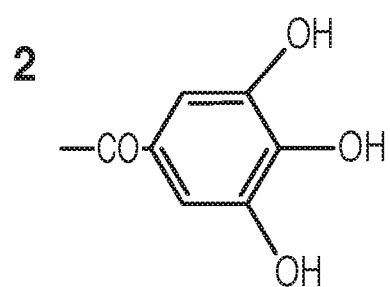
FIG. 1B is a chemical domain structure (2) of one embodiment of R1 shown in FIG. 1A.

In one embodiment, tea catechin is used in accordance with the present inventions (FIG. 1A) wherein $R_1$ may represent H or OH and $R_2$ may represent H or the chemical structure shown in FIG. 1B. In preferred embodiments, green tea (*Cameilia sinensis*) catechins are used. In other embodiments, epicatechin, epicatechin gallate, and gallocatechin (including derivatives thereof) are used. In more preferred embodiments, combinations of the catechins disclosed herein are used. In a most preferred embodiment, epigallocatechin gallate is used.

An exemplary starting source of tea catechins is Polyphenon 100® (Mitsui Norin Co., Tokyo, Japan). It comprises gallocatechin 1.44%, epicatechin 5.81%, epigallocatechin 17.57%, epicatechin gallate 12.51%, and epigallocatechin gallate 53.90%. Another exemplary starting source is Polyphenon E® (Mitsui Norin Co., Tokyo, Japan). It comprises epicatechin 10.8%, epigallocatechin 9.2%, epicatechin gallate 6.5%, epigallocatechin gallate 54.8%, allocatechin gallate 4.0%). These values are the relative percentages of catechins but are not the final concentration in the ointment.

Figure 2:
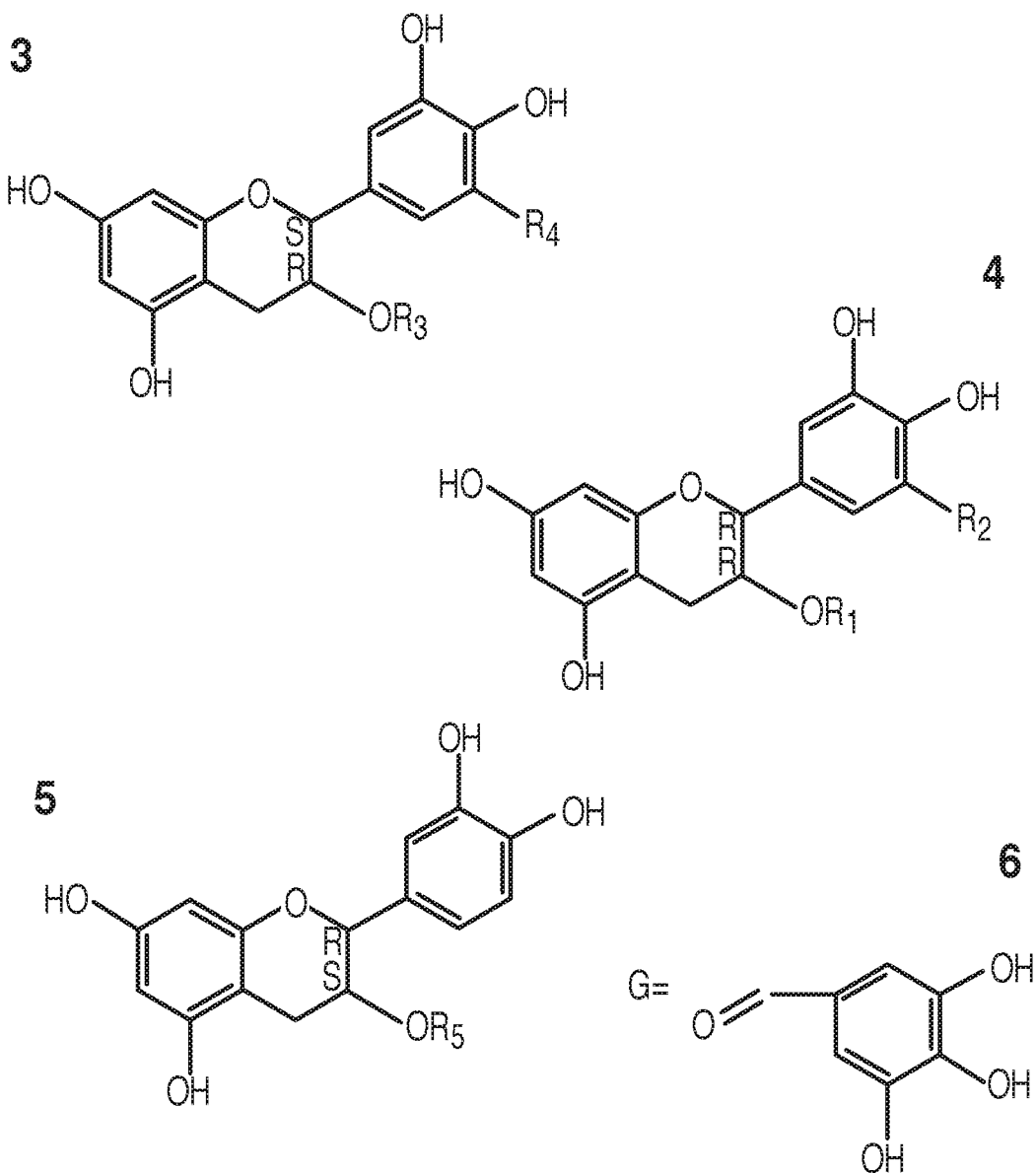
FIG. 2 shows the chemical structures (3, 4, 5) of exemplary catechin molecules known in the art that may be used in accordance with embodiments of the present invention. It also shows the names of multiple catechin molecules for use with the invention. The function al groups that may be inserted at positions R1, R2, R3, R4, and R5 are indicated. Chemical structure 6 shows a function group labeled "G" that may be attached at position R1 or R3 as indicated.

Another exemplary source of catechin used in accordance with the principles of the present invention includes Veregen® (sinecatechins) Ointment, 15% (Medigene AG, Martinsried, Germany). It is a botanical drug product for topical use to treat viral warts (general chemical formula shown in FIG. 2). The water soluble fraction from the green tea leaves comes from plants that may be cultivated to have a great degree of consistency from the extract of the leaves. The FDA may require approval of the source of the plants prior to equivalent drug approval.

The invention provides a method for treating female sexual dysfunctions using catechin percentage by weight that is about 1%-10%. In preferred embodiments, the catechin concentration is between about 2.5%-7.5% by weight. In other preferred embodiments, the catechin concentration is 1%, 2%, 3%, 4%, 5%, 6%, 7%, 8%, 9%, or 10% by weight. In other embodiments, the catechin concentration is between 0.1 and 0.9% by weight. It will be further understood that tea catechins, including green tea catechins, or any other suitable catechin-based or catechin-derived compound is used in accordance with the principles of the present invention at the above-referenced concentrations. For example, a third catechin preparation, formulated by the inventor, may be used if desired. This third preparation was used in connection with many of the patient examples herein which was a 5% green tea ointment preparation, in which 5 grams of a 100-gram tube was comprised of 90% green tea catechin polyphenols. It was compounded and formulated by Custom Scripts Pharmacy of Wesley Hills, Fla.

The specific active ingredient(s) in this drug substance is not identified and the entire drug substance is determined to be active.

In addition, in some embodiments of the invention, Oil of Peppermint NF from 0.1 to 1%, other similar flavor, olfactory or warming compounds may be added to the formulation of the present invention for added stimulatory effect and improved esthetics including improved taste and smell of the catechin product.

The main active ingredient in Veregen® is sinecatechin polyphenols, which is a partially purified fraction of the water extract of green tea leaves from Camellia Sinensis and is a mixture of catechins and other green tea components. Inactive components of Veregen® ointment include: isopropyl myristate, white petrolatum, cera alba (white wax), propylene glycolpalmitostearate, and oleyl alcohol. Catechins constitute 85 to 95% (by weight) of the total drug substance which includes more than 55% of Epigallocatechin gallate (EGCg), and other catechin derivatives such as Epicatechin (EC), Epigallocatechin (EGC), Epicatechin gallate (ECg), and some additional minor catechin derivatives i.e., Gallocatechin gallate (GCg), Gallocatechin (GC), Catechin gallate (Cg), and Catechin (C) in varying amounts. In addition to the known catechin components, it also contains gallic acid, caffeine, and theobromine which together constitute about 2.5% of the drug substance. The remaining amount of the drug substance contains undefined botanical constituents derived from green tea leaves.

In some embodiments, Epigallocatechin gallate (EGCg) may constitute from about 45-%-95% of the active catechin ingredient. The ointment may also include one or more of the following compounds: isopropyl myristate, white petrolatum, cera alba (white wax), propylene glycol palmitostearate, and oleyl alcohol analogous to Veregen®. However, it will be understood that the active catechins may be formulated with different suitable preservatives, extending agents, emulsifiers, dispersing agents, suitable surfactants, an excipient, and in a time release formulation using techniques known in the art.

In one embodiment, 5% catechin ointment as described herein is applied as a thin layer substantially covering the affected area of the external genital organs. In other embodiments, the ointment is applied once. In other embodiments, the ointment is applied several times daily, daily, weekly, monthly, or on an as-needed basis. In yet other embodiments, the ointment is applied for a period of about 1 week, 1, 2, 3, 4, 5, 6, 7, 8, 9, 10, 11, or 12 months. For use to improve libido, without any other underlying FOD symptoms, the compounds of the present invention may generally be applied to the area around and into the vaginal introitus, clitoris and/or labia as desired by the user for maximum effect. In some embodiments, suppositories or douches as is known in the art may be used as further described below. Patient studies indicate once daily use in many instances is sufficient for clinical efficacy. However, some cases may require multiple daily applications. In yet other cases, the catechin ointment may be applied every other day, twice weekly or at another interval to achieve the desired clinical results without adverse reaction (e.g., skin irritation).

For example, about 1.0 to 1.5 cm of ointment may be applied to the affected area one-three times daily. It may be used up to about 4 months or indefinitely without interruption. Mild local skin reactions are not uncommon and initial adverse reactions tend to decrease over the course of treatment.

Figure 3:
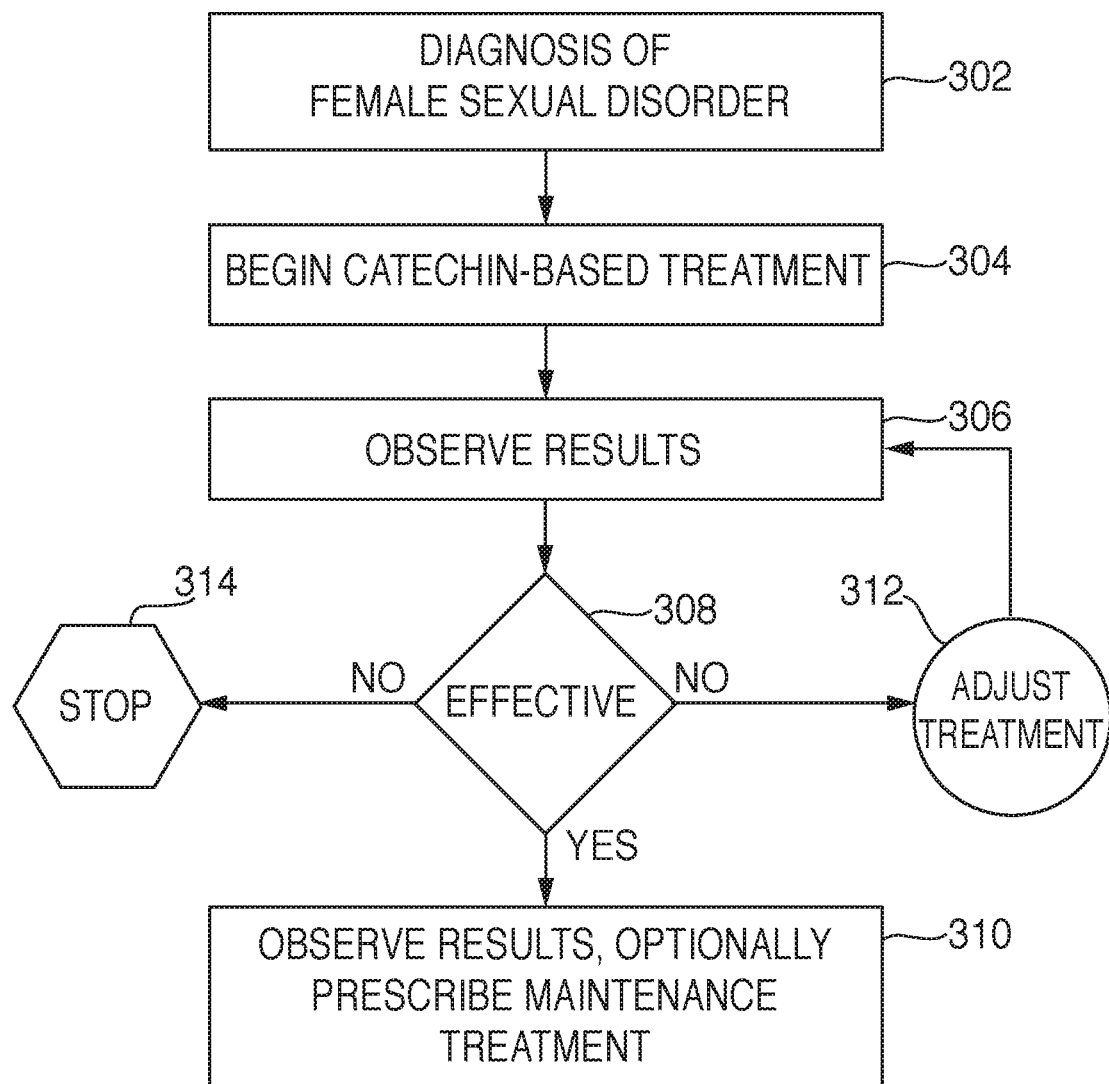
FIG. 3 is a flow chart illustrating an exemplary treatment regimen using the catechin preparations of the invention.

One method of treatment in accordance with an aspect of the present invention is illustrated the flow chart 300 of FIG. 3. As shown at step 302 a patient may be clinically diagnosed with a Female Sexual Disorder. Where medically indicated, appropriate confirmatory testing may be performed (e.g., vaginal pH test, epithelium maturation index, cultures for bacteria and or yeast, and if medically indicated, biopsy). At step 304, a health care provider may prescribe a catechin-based treatment of the type described herein. Initially, this is typically in the 2.5%-7.5% by weight range. Treatment instructions may include the application of the catechin-based ointment once a day for a period of about one month. The catechin ointment may be applied at bedtime or after bathing in the morning. Generally speaking, bathing soon after application of the catechin ointment of the present invention is not optimal as it may be washed off before ample absorption. Certain embodiments, however, may be formulated for fast acting absorption and washing may occur at a reasonable time thereafter.

It will be understood the treatment duration described above is merely exemplary, and others may be used as appropriate. For example, the treatment duration may vary based on patient specifics such as degree of severity of condition, which condition(s) are present, age, physiological specifics, etc. Furthermore, the concentration of the medication may also vary based on the same or similar considerations including skin sensitivity and severity of the underlying condition (e.g., about 2%, 5%, 7.5%, or 10%).

After the initial treatment period, the patient may return to the healthcare provider to observe the results of the treatment (step 306). Depending on these results, further treatment may be prescribed or additional diagnosis performed (step 308). This may include altering diagnosis and changing treatment, continuing treatment, or if the result is an acceptable outcome, tapering or possibly terminating treatment. If the patient is without any substantial adverse effects and is benefiting from the treatment, it may be continued substantially indefinitely.

In the case where additional treatment is appropriate, the health care provider may continue for another period of time and observe results again, in an iterative fashion. Moreover, once "primary" treatment is complete, with desired clinical results, it may be desirable to continue treatment in a secondary fashion by the use of maintenance products (step 310). Such maintenance products may include feminine hygiene soaps, washes, lubricants or other products that contain a lower amount of catechins suitable for long term use and continued clinical efficacy. This may include catechins in the amount of about 1-5% by weight catechin. These products may be used daily or periodically to maintain the desired results.

For example, one treatment protocol in accordance with the present invention may include, after diagnosis, primary treatment with a 5% by weight catechin-based ointment for 2-8 weeks, followed by continued secondary treatment, if appropriate, with a feminine wash, soap or lubricant of about 1-3% by weight catechin for several times per week for an extended period or as needed for maintenance (which, in some cases may be long term). Such a diagnosis and treatment plan may, in some instances, be prescribed at the initial patient visit and diagnosis, with secondary treatment following the resolution of primary symptoms. In this case, steps 306 and 308 above may be omitted or may occur after secondary treatment step 310 has begun.

For some patients that have noted habituation to the treatment, an increase in the concentration or frequency of treatment may be instituted. For example, maintenance treatment may require an increase in the percentage of catechin depending upon a subject's individual response and/or tolerance. For example, and increase from 5% to 10% catechin by weight may be indicated.

Embodiments of the invention are also contemplated for over the counter ("OTC") applications. For example, catechin preparations of the present invention may be formulated with active ingredients that allow it to be sold OTC. In this instance, the manufacturer may describe the symptoms and/or desired results of certain afflictions, and instruct a user to apply an effective amount of the preparation for a certain period of time. If the symptoms resolve, the manufacturer may instruct the user to continue, discontinue or taper treatment (e.g., maintenance or secondary treatment described herein), and if not, seek further assistance from a medical professional.

The formulations of the invention might comprise additional active ingredients or flavor enhancers. Examples include compounds, extracts or essential oils from one or more of the following sources: ascorbic acid, vitamin E, omega 3, salt water, menthol, agar essential oil, agar extract, ajwain, aloe vera, amyris, angelica root, anise, balsam, basil, bay rum, bergamot, black pepper, buchu, butterbur, cajeput, cannabis flower, caraway, cardamom seed, carrot seed, cedarwood, Cedarleaf, chamomile, cinnamon, cistus, citrus vulgaris, citronella, clary sage, clove leaf, coriander, costmary, cranberry seed, cumin/black seed, cypress, davana, dill, eucalyptus, fennel seed, fenugreek, frankincense, galbanum, geranium, ginger, grapefruit, grape seed (e.g. Vitis vinifera), henna, jasmine, juniper berry, lavender, lemon, lemongrass, lime, litsea cubeba, lobelia/neem, melissa (Lemon balm), mentha arvensis/Mint, mugwort, mustard, myrrh, neroli, nutmeg, orange, oregano, orris, parsley, patchouli, perilla, pennyroyal, peppermint, pine, rose, rosehip, rosemary, rosewood, sage, sandalwood, sassafras, savory, schisandra, spearmint, star anise, tarragon, tea tree, thyme, vetiver, yarrow ylang-ylang, and other herbs, natural flavorings, or artificial flavorings known in the art.

The concentration of lemon oil in the formulations of the invention may vary so long as it is sufficient to provide long-acting relief for nasal inflammation and allergies. Thus, the concentration of lemon oil may be about 0.10% to 10% v/v lemon oil. In preferred embodiments, the concentration may be about 0.10%, 0.20%, 0.30% 0.40%, 0.5%, 0.60%, 0.70%, 0.80%, 0.90%, or 1.0% v/v. In particularly preferred embodiments, the lemon oil concentration is 0.24% or 0.48% v/v. In other preferred embodiments, the concentration may be between about 1.0% to 2.0%, 2.0% to 3.0%, 3.0% to 4.0%, 4.0% to 5.0%, 5.0% to 6.0%, 6.0% to 7.0%, 7.0% to 8.0%, 8.0% to 9.0%, or 9.0% to 10.0% v/v, or increments therebetween.

The formulations of the invention comprise an emulsifier or surfactant. In some embodiments, the concentration of the emulsifier is about 1.0% to 10% v/v. In preferred embodiments, the concentration may be about 1.0% to 2.0%, 2.0% to 3.0%, 3.0% to 4.0%, 4.0% to 5.0%, 5.0% to 6.0%, 6.0% to 7.0%, 7.0% to 8.0%, 8.0% to 9.0%, or 9.0% to 10.0% v/v, or increments therebetween. In a more preferred embodiment, the concentration is about 3.0%.

Emulsifiers for pharmaceutical, nutraceutical, and other human consumption are well-known in the art. Exemplary emulsifiers for use in the formulations of the invention include food emulsifiers such as egg yolk (lecitihin), mustard (mucilage), soy lecithin, pickering stabilization, sodium stearoyl lactylate, and DATEM (Diacetyl Tartaric Acid Ester of Monoglyceride) and anise. Other emulsifiers include emulsifying wax, cetearyl alcohol, polysorbate 20, and ceteareth 20.

The formulations of the invention comprise alcohol as surfactant or penetration enhancer. In some embodiments, the concentration of alcohol is about 1.0% to 10% v/v. In preferred embodiments, the concentration of alcohol may be about 1.0% to 2.0%, 2.0% to 3.0%, 3.0% to 4.0%, 4.0% to 5.0%, 5.0% to 6.0%, 6.0% to 7.0%, 7.0% to 8.0%, 8.0% to 9.0%, or 9.0% to 10.0% v/v, or increments therebetween. In a more preferred embodiment, the concentration is about 3.0%. Exemplary alcohols include ethanol, isopropyl alcohol, and benzyl alcohol.

Other embodiments of the present invention may include certain other active ingredients to treat the afflictions described herein. For example, low doses of hormones, SERMs, and/or vitamins may be included, if desired for an improved treatment response. For example, the 5% catechin preparation described herein may include about Vitamin E, about 0.001.0-1% estrogen and/or if FDA approved about 0.001-0.01% testosterone. A specific example may include about 5% catechin by weight, about 0.01% or less estradiol, estriol, estrone and vitamin E. Another embodiment may include about 5% catechin, combined with lower doses of oral medications such as estrogens or Ospemifene. Combinations of any of the above may combined together in one topical formulation. The catechin ointment can be used as an "estrogen sparing" agent lessening the chance of adverse effects from estrogen therapeutics.

The present invention may also be suitable for internal use, for example, through ointment or other application vectors such as suppository or douche. Such uses may require additional FDA approval. In the case of vaginal suppository the content of tea catechin may be around 100-500 mg/capsule, in some embodiments about 200-300 mg/capsule, and in one specific embodiment a 250 mg/capsule. Of note tea catechin suppositories have the added benefit of reducing uterine fibroids and cervical dysplasia.

Another embodiment of the present invention may include a douche having a solution including a catechin preparation at the concentrations of the invention as disclosed herein. In some embodiments, the douche solution may include a suitable surfactant so the active ingredients remain attached to the affected internal areas for a period of time after use. In other embodiments, the douche solution comprises time-release formulations such that the solution need only be introduced periodically (i.e., every several days or weekly).

A typical usage example for the suppository in the case where for example the affected area is the cervix or the vagina is to insert a capsule containing 100-500 mg tea catechin, from once to several times every day for a period of 1-2 months. A douche may be used every other day, or twice a week, or periodically as indicated for 1-2 months depending on surfactant used.

It will be understood that other feminine hygiene and lubricant products may also be manufactured that include tea catechins for regular use to obtain the benefits of the present invention. For example, a lubricant such as K-Y Jelly® (Reckitt Benckiser, Parsippany, N.J.), or other personal lubricant as known in the art, may include 1-10% by weight catechins as well as certain soap or wash formulations. These may be used, during, after (or before) the treatment regimens described herein to increase or maintain their benefits. In some embodiments, they also may be sold as OTC products that may be used without consulting a health care provider.

It will be further understood that time release formula may be achieved using any suitable method including the use of esters to achieve the desired application of active ingredient. Thus, in some embodiments, time release formulations comprise formate, acetate, propionate, phenylpropionate, butyrate, valerate, hexanoate, caproate, isocaproate, heptanoate, enanthate, octanoate, cypionate, nonanoate, decanoate, or undecanoate.

In preferred embodiments, shorter esters such as formate, acetate, and propionate are used for ointments, feminine wash and lubricants which are applied frequently. In other preferred embodiments, longer esters such as enanthate and cypionate are used for products applied less frequently such as suppositories and douches.

Further, health care professionals should be cognizant of the difference that large systemic doses of catechins may have. For example, a man taking several herbal substitutes for weight loss with included 400 mg epigallocatechin-3-gallate, EGCG, daily developed acute but reversible liver failure. As a result, the United States Pharmacopeia have suggested, but not mandated, a warning, stating symptoms of liver injury be placed on any green tea extract monograph produced.

Alternatively, data support that moderate systemic doses of catechins derived from green tea provide a protective role against the risk of ovarian and endometrial cancers. Green and black tea have shown therapeutic benefit in relation to gynecologic cancers. The topical application of green tea catechins (e.g., Veregen) to the external genitalia have proven safe and effective dosed three times daily for four months.

The invention provides a method for treating a female sexual disorder comprising administering an effective amount of a pharmaceutical comprising between 1% and 10% catechin to an individual that suffers from the disorder.

An "effective amount" refers to an amount of therapeutic compound that is effective, at dosages and for periods of time necessary, to achieve the desired therapeutic or prophylactic result. A "therapeutically effective amount" of a therapeutic compound may vary according to factors such as the disease state, age, sex, and weight of the individual. A therapeutically effective amount may be measured, for example, by improved survival rate, more rapid recovery, or amelioration, improvement or elimination of symptoms, or other acceptable biomarkers or surrogate markers. A therapeutically effective amount is also one in which any toxic or detrimental effects of the therapeutic compound are outweighed by the therapeutically beneficial effects. A "prophylactically effective amount" refers to an amount of therapeutic compound that is effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

An "individual," "subject" or "patient" is a vertebrate. In certain embodiments, the vertebrate is a mammal. Mammals include, but are not limited to, primates (including human and non-human primates) and rodents (e.g., mice, hamsters, guinea pigs, and rats). In certain embodiments, a mammal is a human. A "control subject" refers to a healthy subject who has not been diagnosed as having a disease, dysfunction, or condition that has been identified in an individual, subject, or patient. A control subject does not suffer from any sign or symptom associated with the disease, dysfunction, or condition.

A "medicament" is an active drug that has been manufactured for the treatment of a disease, disorder, or condition.

"Patient response" or "response" can be assessed using any endpoint indicating a benefit to the patient, including, without limitation, (1) inhibition, to some extent, of disease progression, including stabilization, slowing down and complete arrest; (2) reduction in the number of disease episodes and/or symptoms; (3) inhibition (i.e., reduction, slowing down or complete stopping) of a disease cell infiltration into adjacent peripheral organs and/or tissues; (4) inhibition (i.e. reduction, slowing down or complete stopping) of disease spread; (5) decrease of an autoimmune condition; (6) favorable change in the expression of a biomarker associated with the disorder; (7) relief, to some extent, of one or more symptoms associated with a disorder; (8) increase in the length of disease-free presentation following treatment; or (9) decreased mortality at a given point of time following treatment.

As used herein, a "pharmaceutically acceptable carrier" or "therapeutic effective carrier" is aqueous or nonaqueous (solid), for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of specific inhibitor, for example, carbohydrates, such as glucose, sucrose or dextrans, antioxidants such as ascorbic acid or glutathione, chelating agents, low molecular weight proteins or other stabilizers or excipients.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

The invention provides effective routes for catechin administration. In preferred embodiments, effective routes of drug administration include transdermal, topical, and vaginal, modes.

Exemplary drug formulations of the invention include aqueous solutions, organic solutions, powder formulations, solid formulations and a mixed phase formulations. The pharmaceutical compositions may contain any conventional, non-toxic, pharmaceutically-acceptable carriers, adjuvants or vehicles.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts retain the desired biological activity of the therapeutic composition without toxic side effects. Examples of such salts are (a) acid addition salts formed with inorganic acids, for example, hydrochloric acid, hydrobromic acid, sulfuric acid, phosphoric acid, nitric acid and the like/and salts formed with organic acids such as, for example, acetic acid, trifluoroacetic acid, tartaric acid, succinic acid, maleic acid, fumaric acid, gluconic acid, citric acid, malic acid, ascorbic acid, benzoic acid, tanic acid, pamoic acid, alginic acid, polyglutamic acid, naphthalenesulfonic acid, naphthalene disulfonic acid, polygalacturonic acid and the like; (b) base addition salts or complexes formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethlenediamine; or (c) combinations of (a) and (b), e.g. a zinc tannate salt and the like.

The compositions may conveniently be administered in unit dosage form and may be prepared by any of the methods well-known in the pharmaceutical art, for example, as described in Remington's Pharmaceutical Sciences, 17th ed., Mack Publishing Co., Easton, Pa. (1985), incorporated herein by reference in its entirety.

In certain embodiments for transdermal administration, delivery across the barrier of the skin would be enhanced using electrodes (e.g. iontophoresis), electroporation, or the application of short, high-voltage electrical pulses to the skin, radiofrequencies, ultrasound (e.g. sonophoresis), microprojections (e.g. microneedles), jet injectors, thermal ablation, magnetophoresis, lasers, velocity, or photomechanical waves. The drug can be included in single-layer drug-in-adhesive, multi-layer drug-in-adhesive, reservoir, matrix, or vapor style patches, or could utilize patchless technology. Delivery across the barrier of the skin could also be enhanced using encapsulation, a skin lipid fluidizer, or a hollow or solid microstructured transdermal system (MTS, such as that manufactured by 3M), jet injectors. Additives to the formulation to aid in the passage of therapeutic compounds through the skin include prodrugs, chemicals, surfactants, cell penetrating peptides, permeation enhancers, encapsulation technologies, enzymes, enzyme inhibitors, gels, nanoparticles and peptide or protein chaperones.

One form of controlled-release formulation contains the therapeutic compound or its salt dispersed or encapsulated in a slowly degrading, non-toxic, non-antigenic polymer such as copoly(lactic/glycolic) acid, as described in the pioneering work of Kent et al., U.S. Pat. No. 4,675,189, incorporated by reference herein. The compounds, or their salts, may also be formulated in cholesterol or other lipid matrix pellets, or silastomer matrix implants.

One embodiment of the present invention may be used as a topical ointment for the treatment of Female Sexual Disorders including genitopelvic/pain disorder; sexual interest/arousal disorder; female orgasmic disorder, VVA and other vulvovaginal disorders including but not limited to vestibulodynia. For ointment preparations, the content of catechin may be between about 2.5%-7.5% weight.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topical transdermal patches are also included in this invention.

Dosage levels of between about 0.01 and about 100 mg/kg body weight per day, preferably 0.5 and about 50 mg/kg body weight per day of the active ingredient compound are useful in the prevention and treatment of disease. Such administration can be used as a chronic or acute therapy. The amount of drug that may be combined with the carrier to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, gender, diet, time of administration, rate of excretion, drug combination, the severity and course of an infection, the patient's disposition to the infection and the judgment of the treating physician.

In order that the invention described herein may be more fully understood, the following examples are set forth. It should be understood that these examples are for illustrative purposes only and are not to be construed as limiting this invention in any manner.

Example Set 1

Aspects present invention will be explained in more detail with reference to the following examples, which are in no way meant to limit the scope of the invention. The first two examples were the initial patients tested. Based on the initial results of these two test subjects (Set 1), a more detailed pilot study (Set 2) was then conducted to further quantify and better understand the scope and efficacy of the present invention with respect to a reasonably diversified patient base. It was during the initial testing of the first two patients in Set 1 that libido increase was discovered.

Initial clinical tests of the present invention were carried out in private practice in Rockland County, N.Y. with two women who had been diagnosed with VVA, vestibulodynia, Genital Pelvic Pain Disorder (GPPD) and Sexual Interest Arousal Disorder (SIAD).

Tests were performed on these patients using a Catechin Green Tea Ointment, 15% by weight catechin (Custom Scripts Pharmacy Wesley Hills, Fla.) applied to the affected external genital organs continuously once a day for 2-10 weeks and intermittently for up to one year. During that period of monthly treatment examinations of the affected areas were conducted.

Patient 1. Post-menopausal 62-year-old female with atrophic vaginitis and a prior long history pre-menopausally of vestibulodynia. After menopause, intercourse was not possible because of pain in the vaginal introitus and decrease in vaginal lubrication within the vagina, symptoms typical of vulvovaginal atrophy. Clinically, there was evidence of decreased vaginal lubrication and erythema around the posterior forchette with pain elicited with Q-tip palpation on exam.

After initially applying samples of Veregen for a week and noting benefit patient was switched to Green Tea Ointment, 15% (Custom Scripts Pharmacy) for two weeks once daily, the patient noted increase in vaginal mucous and noticeable decrease in pain in the vaginal vestibule thereby allowing intercourse to be pain free. Despite decrease in vestibular pain, however, she complained of some irritation and superficial desquamation of her vaginal mucosa and was switched to 5% Green Tea Ointment (Custom Scripts Pharmacy, Wesley Chapel, FA). A follow-up exam revealed a normal vaginal mucosa with increased vaginal lubrication, no erythema around the posterior forchette, and no pain was elicited with Q-tip palpation. She had no complaints of irritation. She noted increases in her sexual desire that was maintained for over one year while using the 5% Green Tea Ointment. The patient continues to use Green Tea Ointment, 5% (Custom Scripts Pharmacy) intermittently, applying approximately 0.5 cm daily for a week at a time when she notes reoccurrence of symptomology. She has been followed for over a year.

Patient 2. Patient 2 (SG) was unable to have intercourse and suffered from chronic genital pain. SG is a 68 y/o female who was followed by her gynecologist for the past 11 years prior to using 15% GTO. She had a normal menarche, 3 children delivered vaginally, and essentially no significant issues during her reproductive years. She developed menopausal symptoms in her early 40s and was started on low dose PREMPRO and continued on that regimen through 2004. At that point she became increasingly nervous about taking hormones and the decision was made to attempt changing to a bio-identical regimen of hormones. After a year, she wanted to switch back to PREMPRO because she felt much better on that regimen and was experiencing increasing hot flashes, vaginal dryness and loss of libido on the bio-identicals. Low dose PREMPRO (0.3/1.5) was started and VAGIFEM was used for vaginal issues. She maintained this regimen and felt fairly good, despite no libido, until 2011 at which time she developed a benign breast lump and decided to stop all hormonal therapy. Her vagina became increasingly dry, sensitive and ultimately painful. Intercourse was essentially nonexistent due to her pain, and she presented late in 2014 wanting to address this issue. Examination at that time revealed an atrophic vulva and vagina, mucosa was very dry and flat with some scarring at the perineum and skin changes consistent with Lichens Sclerosis. Green Tea Ointment, 15% catechin (Custom Scripts Pharmacy) was prescribed and lubrication issues reviewed in detail.

PMH: Sulfa allergy

Hx of osteoporosis, carpal tunnel syndrome

Medications: Evista

Significant Family hx: Ovarian Cancer in her maternal Grandmother

Patient 2 returned approximately 10 weeks after starting the Green Tea Ointment, 15% catechin using 0.5 inches of material to vulva up to once daily her vulvar pain was gone and there was a noticeable improvement in her vaginal dryness. After two weeks she attempted intercourse several times but was unable to have vaginal penetration because of dyspareunia. Patient 2, however, demonstratively expressed that this regimen had changed her sexuality potential and her life in general because her arousal and desire had increased. The exam showed marked improvement in the skin around the perineal body, no tenderness, and healthy-appearing vaginal mucosa. Lubrication issues were again reviewed and a natural Vitamin E suppository was prescribed for additional help with lubrication. Subsequently, the patient did not request a renewal of the 15% Green Tea Ointment and was lost to follow-up.

Example Set 2

Based on the results of the above testing, additional test subjects were recruited at random to further test efficacy and scope of the invention. Treatment with 15% by weight catechin preparation caused irritation and was not suitable for long term use. The benefits of treatment were mitigated. A custom catechin preparation was formulated at 5% which was much better tolerated. Some patients were referred from gynecologic healthcare professionals or from medical dermatology practice, primarily for complaints of genitopelvic pain disorder (GPPD), including dyspareunia and vulvodynia. The initial two subjects (Set 1) showed improvement not just in alleviation of genitopelvic pain (GPPD), but also in interest and arousal (SIAD). Questionnaires were then introduced in this test Set 2 to elucidate whether these added therapeutic effects would be seen in other women whose primary complaint was dyspareunia or vulvodynia. The questionnaires were known in the art. (See DeRogatis et al., *J. Sex Med* 5:357-364 (2008); DeRogatis et al., *J. Sex Med* 6:175-183 (2009) Rosen et al., *J. Sex & Marital Therapy,* 26:2, 191-208 (2000); Symonds et al., *J Sex Med* 4:1328-1335 (2007). The foregoing are incorporated by reference in their entirety.) In addition, a questionnaire was used that is provided at FIGS. 5A to 5C.

The test subjects were not recruited for, nor did they complain of, low libido symptoms. Test subjects were not told the present invention may have an effect on sexual arousal, desire or orgasm. It was understood, however, by the subjects that the catechin preparations of the present invention may (or may not) help relieve symptoms of genitopelvic pain/penetration (GPPD). Patients were a mix of premenopausal and postmenopausal women. The age range was from 38 to 68 years old.

Test Parameters and Details

Compounding Pharmacy: Custom Scripts Pharmacy compounded and supplied the prescribed 5% Green Tea Ointment ("GTO"). It comprised 90% polyphenols from the water soluble fraction of green tea. (Pharmacy Compounding Centers of America, Houston Tex.) It was formulated in petrolatum USP with no additives. The medication was supplied in a white opaque tube with 30 grams per tube from Custom Scripts Pharmacy.

Subjects read, discussed and then signed a consent form for enrollment into the study, a consent form for use of their clinical photographs, a non-disclosure agreement, and an instruction sheet for use of GTO. They were asked to complete several standard questionnaires prior to use of the study medication.

All patients were up to date and instructed to continue their regular gynecological care as recommended by their gynecologic healthcare professional. Physical examinations were performed by Wendy Epstein, M.D., F.A.A.D. along with her medical assistant. Pain was confirmed by Q-tip palpation of affected sites. Some of the postmenopausal subjects had a maturation index and vaginal pH taken before and after 4 weeks of GTO daily use. Most of the premenopausal subjects had a pre and post vaginal pH measured.

Vaginal maturation index: is an indication of estrogenic effect on the vaginal epithelium. The test was done, in postmenopausal subjects, to demonstrate that the mechanism of action of GTO is independent or void of any estrogenic effects and therefore safe for women who for a variety of medical or personal choice issues cannot or will not use estrogenic compounds or other hormones to treat their sexual disorder. A brushing of the lateral vaginal wall was, spread on a glass slide, fixative applied immediately and the sample allowed to dry then sent for evaluation of the vaginal maturation index to either Quest Diagnostics or LabCorp.

Vaginal pH as another indication of estrogenic state was done using pH paper calibrated from 5.5-8.0

The Female Sexual Function Index (FSFI) is a known standard questionnaire, designed and validated for assessment of female sexual function and quality of life in clinical trials or epidemiological studies. It is a multidimensional self-reporting measure of female sexual function designed to be a clinical trials assessment instrument. The 19-item assessment of overall sexual function is divided into 6 domains: desire, subjective arousal, lubrication, orgasm, satisfaction, and pain. Every domain contributes a maximum of six points to the total score; thus the maximal score is 36. Higher scores indicate better sexual function. Significant and positive statistical differences have been observed in each domain between controls and women with female sexual arousal disorder. It has proven a valid indicator in the assessment of key dimensions of female sexual function. However, the FSFI is appropriately used only for subjects who have had some level of sexual activity during the measurement period.

The Sexual Distress Scale-Revised (FSDS-R) is a known standard questionnaire to assess the frequency of personal distress that a woman may have been experiencing because of a sexual dysfunction during the past 30 days. It helps quantify the extent to which the sexual dysfunction is causing her emotional distress. It was developed to provide a standardized, quantitative measure of sexually related personal distress in women. The questionnaire was originally designed to validate a diagnosis of hypoactive sexual desire disorder which required a woman to be distressed about the lack of desire. Question 13 specifically assesses distress due to low sexual desire. The questionnaire was used more generally to validate that a woman has distress caused by any of the three disorders of female sexuality despite the lack of specific questions about pain or discomfort.

The 13 items are rated on a 5-point scale from 0 (never) to 4 (always); thus, the total score ranges from 0 to 52, with lower scores indicating less distress. A score of >11 indicates Female Sexual Dysfunction.

The Vulvovaginal Symptom Questionnaire (VSQ) is a known standard questionnaire more specifically addresses female genitopelvic pain penetration disorders (GPPD's). (See Erekson, Elisabeth A. et al. "The VSQ: A Questionnaire to Measure Vulvovaginal Symptoms in Postmenopausal Women." Menopause (New York, N.Y.) 20.9 (2013): 973-979. PMC. Web. 17 Mar. 2016.) The questionnaire's focus is to determine the nature and effect of a woman's vulvar symptoms. The VSQ is a 21-item written questionnaire with four scales: symptoms, emotions, life impact, and sexual impact.

Sexual Activity Log (SAL) is a known standard questionnaire, tries to quantify the level of sexual desire experienced, the level of distress about the level of sexual desire experienced, the number of sexual activities, whether the sexual activity was satisfying, i.e. did the woman experience an orgasm. The SAL questionnaire was answered prior to beginning the study and at the end of each one of the four weeks during the one-month study. Following the one-month study period, subjects were allowed to continue the 5% GTO. The effects continued. Some individuals desired and tolerated higher concentrations of GTO 7.5% after several months of daily use.

Patient's Global Impression of Improvement (PGI-I) was used to assess women's evaluation of the overall change in their SIAD or GPPD. It comprised one question: "How is your condition (i.e., decreased sexual desire or pain or discomfort and feeling bothered by it) today compared with when you started study medication?" and was rated on a 7-point scale from 1 (very much improved) through 4 (no change) to 7 (very much worse).

Patient Benefit Evaluation (PBE) was a simple question with a Yes or No response to whether the medication was useful for them after one month of usage. "Overall, do you believe that you have experienced a meaningful benefit from the study medication?"

The Narrative Questionnaire was developed with questions focused primarily on characterizing the nature of a woman's genitopelvic pain disorder, its impact on her emotional and sexual life and later on the benefit, if any, from the study medication.

Participants are allowed to complete all questionnaires alone, in a private room. There were then given 5% catechin-based Green Tea Ointment (5% GTO), formulated by Custom Scripts Pharmacy green tea water soluble extract in petrolatum (to use once daily according to the instruction sheet. They were asked to fill out the SAL weekly. At the end of the four weeks the subject returned, filled out questionnaires and was examined with repeat pH and vaginal maturation index if indicated.

Two of the subjects were premenopausal asymptomatic women with no complaints of sexual disorders.

Test Set 2 Patient

1. Patient PD

Presenting Complaint: PD was a 61-year-old post-menopausal woman with (GPPD) Genitopelvic Pain Disorder pain (dyspareunia) secondary to Vulvovaginal atrophy (VVA), with decreased lubrication and decreased sexual desire (interest) and arousal (SIAD) Sexual Interest/Arousal Disorder.

Benefit realized: After using 5% GTO for one month, PD noted decreased vestibulodynia, vulvodynia and dyspareunia (GPPD). Unexpectedly, she noted an increase in her level of sexual desire and arousal and an increase in her orgasms.

Past Medical History: History of breast cancer.

Characterization of Pain: This 61-year-old Italian fair complexion Caucasian 12 years post-menopausal woman with a history of breast cancer prior to use of the study medication had experienced 1-5 years of burning and soreness always during and after intercourse which was rated as significant to severe pain located primarily on the left side of the vaginal introitus and left inner labia. The pain, dyspareunia, prevented intercourse with her husband causing her to feel guilty. The pain was a significant factor for why she was not having intercourse. She rarely became lubricated and always required use of lubricant. She was, however, able to have an orgasm most of the time but only sometimes during intercourse. She only felt sexual desire about once a month and was constantly distressed about her sexual life.

After using the 5% GTO, for two weeks, she almost never had pain or discomfort and if she did it was mild to moderate during intercourse. Most of the time she had absolutely no discomfort during vaginal penetration and was able to become lubricated most of the time. She continued to have an orgasm most of the time. Her sexual desire increased to once a week from a desire of less than one time per month, and she always became aroused during sexual activity. The "use of the medication seems to allow an orgasmic feeling during routine activities." After using 5% GTO she was seldom distressed about her sexual life.

Female Sexual Function Index (FSFI questionnaire) results after 4 months (patient had noticeable effects within one month (see SAL) but was delayed in filling out forms) of using 5% Catechin-based GTO were as follows:

|  | BEFORE | AFTER |
| --- | --- | --- |
| Desire: | 1.8 | 4.8 |
| Arousal | 2.1 | 5.7 |
| Lubrication | 2.1 | 5.7 |
| Orgasm | 2.4 | 5.6 |
| Satisfaction | 2.8 | 6.0 |
| Pain | 1.2 | 6.0 |
| TOTALS | 12.4 | 33.8 |

A score of <=26.55 is diagnostic of Female Sexual Dysfunction. Patient had female sexual dysfunction prior to using the study medication and her female sexual dysfunction resolved after using the 5% green tea ointment without any adverse effects. Patient had a significant increase in all parameters, notably in her sexual desire, arousal, lubrication, orgasm satisfaction and decrease in pain.

Patient Global Impression of Improvement scored the highest with "Very much improved"

Patient Benefit Evaluation: "Overall do you believe that you have experienced a meaningful benefit from the study medication?" Answer: Yes.

Sexual Activity Log SAL:

Prior to using catechin-based GTO 5%, subject had no desire, was extremely distressed because of low sexual desire, had not had any sexual activity in the prior week and did not have an orgasm. After one week after using the study medication, she noted low desire and was still extremely distressed by this and had no orgasm or any sexual activity. After two weeks of using 5% GTO, she noted moderate desire, was only moderately distressed about her level of desire and had one satisfying sexual activity with achieving an orgasm. At the end of week three she had moderate desire was only a little bit distressed about her level of desire and had two satisfying sexual activities with orgasms. At the end of four weeks of using GTO she had strong sexual desire, was not at all distressed about her level of desire and had three satisfying sexual events with orgasms. Her satisfying sexual activities went from 0 to three (3) along with increase sexual desire and orgasms.

PD stated that she had no problems using the medication and no unpleasant side effects. Patient commented that she had sexually pleasant "orgasmic" feelings when wearing tight jeans and was aware of her spontaneous pleasurable genital sensations.

Sexual Distress Scale-Revised:

A score of >11 is indicative of Female Sexual Distress. Prior to use of GTO subject had a score of 46 qualifying her as Female Sexual Distress. After use of the medication, she had a score of 5. She no longer was distressed by her sexual function. Of notable significance, item 13 specifically assesses distress due to low sexual desire. Before using 5% catechin-based GTO, the patient was "Always" bothered by low sexual desire. After using the topical green tea ointment she was "Rarely" was bothered by low sexual desire.

The Vulvovaginal Symptom Questionnaire:

The questionnaire is to determine the nature and effect of a woman's vulvovaginal symptoms. PD's distress significantly decreased from a pre GTO score of 13/21 to 1/21 indicating lack of physical symptoms, emotional concerns, life impact, and sexual impact. This indicated a very positive overall result.

2. Patient DG

Presenting Complaint: DG was a 47-year-old postmenopausal despite taking an oral estrogen (Loestrin Fe), DG had symptoms of vulvovaginal atrophy (VVA) manifested as both decreased in lubrication and dyspareunia, Genitopelvic Pain Disorder (GPPD)

Benefit realized: After using 5% GTO (Veregen 15% GTO mixed with petrolatum for a concentration of 5% GTO) for one month, DG noted a significant increase in her ability to become lubricated; a decrease in her dyspareunia and an unexpected increase in her sexual arousal and desire and orgasm. She continued to use 5% GTO from Custom Scripts Pharmacy for at least another 8 months with continued benefit.

Medications: Bystolic; Diovan; Lo Loestrin Fe; 5% GTO

Summary of Narrative questionnaire: This 47-year-old Italian medium complexion Caucasian 7 years post-menopausal woman prior to use of the study medication had experienced 1-5 years of burning and soreness during intercourse most of the time which was rated as moderate. The pain located particularly on posterior forchette of the vaginal introitus i.e. vestibulodynia and occurred only during direct contact with the area including sometimes with manual touching of the area but most of time with intercourse. She sometimes became lubricated during sexual activity and sometimes required use of lubricant. She was however able to have an orgasm most of the time during sexual activity with her husband. She sometimes felt sexual desire about several times a week but was sometimes distressed about her sexual life because of the provoked pain upon penetration. The sensation of pain was a major contributing factor why she would decline having intercourse despite feeling sexual desire to do so.

After using the 5% GTO, for one week, she no longer had pain or discomfort during intercourse or vaginal penetration. She was always able to become lubricated. She always had an orgasm. Her sexual desire remained often at several times a week and she always became aroused during sexual activity. DG no longer had pain affecting her sexual life. She was seldom distressed about her sexual life. "It (5% GTO) has improved my life tremendously. I am happy my intimacy has improved without having to use (additional) hormones," "My sex life is so much more pleasurable now. As a woman who is post-menopausal, I think this medication and treatment would be so beneficial to women, so they can experience renewed intimacy with their significant other." She rated the medication extremely effective; and no longer experiences any discomfort or pain.

Female Sexual Function Index (FSFI questionnaire) results after 4 months were as follows: (patient had noticeable effects within one month (see SAL) however, she filled out forms after 4 months of continued use of 5% GTO)

|  | BEFORE | AFTER |
| --- | --- | --- |
| Desire: | 2.4 | 5.4 |
| Arousal | 3.9 | 5.4 |
| Lubrication | 3.6 | 5.4 |
| Orgasm | 5.2 | 6.0 |
| Satisfaction | 4.4 | 6.0 |
| Pain | 3.6 | 6.0 |
| TOTALS | 23.1 | 34.2 |

A score of $<=26.55$ is diagnostic of Female Sexual Dysfunction. Patient DG had female sexual dysfunction prior to using the study medication and her female sexual dysfunction resolved after using the 5% GTO without any adverse effects. Patient had a significant increase in most parameters, notably in her sexual desire, arousal, lubrication, satisfaction and decrease in pain. Most notably was her increase in desire and decrease in pain.

Patient Global Impression of Improvement scored the highest with "Very much improved." Patient wrote by hand "great."

Patient Benefit Evaluation: "Overall do you believe that you have experienced a meaningful benefit from the study medication?" Answer Yes.

Sexual Activity Log SAL

Prior to using GTO, DG had strong sexual desire which was maintained throughout the test period. She was a little bit distressed about her level of sexual desire, yet had three sexual activities in the prior week and did have an orgasm. At the end of four weeks of using the 5% green tea ointment she had strong sexual desire, was not at all distressed about her level of desire and had five satisfying sexual events with orgasms in the prior week. The subject had a very active sexual life prior to using GTO but this was further enhanced, much to the patient's amazement, after using GTO. She continues to use GTO for over 9 months with continued satisfaction.

She stated that she had no problems using the medication and no unpleasant side effects.

Sexual Distress Scale-Revised

A score of >11 is indicative of Female Sexual Distress. Prior to use of GTO, subject had a score of 10, one point short of qualifying her as Female Sexual Distress. After use of GTO, she had a score of 4. DG was significantly less distressed by her sexual function after using the 5% green tea ointment primarily because of a resolution of her dyspareunia.

The Vulvovaginal Symptom Questionnaire

The questionnaire is to determine the nature and effect of a woman's vulvovaginal symptoms. The subject's distressed significantly decreased from a pre-GTO score of 7/21 to post-GTO score of 0/21 indicating lack of physical symptoms, emotional concerns, life impact, and sexual impact. Physical symptoms of reduced pain and improved lubrication were the main reasons for this improvement.

3. Patient PF

Presenting Complaint: PF was a 57-year-old postmenopausal woman with symptoms of vulvovaginal atrophy manifested as vestibulodynia, vulvadynia and dyspareunia i.e. genitopelvic pain disorder (GPPD)

Benefit realized: After one month daily use of 5% GTO PF had significant decrease in: Genitopelvic pain/penetration Patient is a 57-year-old fair complexion, red haired Irish Caucasian one year postmenopausal woman, in a long term relationship, who for 1-5 years had moderate burning/soreness some of the time around the entire circumference of her vaginal introitus causing her mild discomfort during vaginal penetration, dyspareunia. She had pain or discomfort most of the time after intercourse with vaginal penetration. Intercourse was the activity that provoked pain. PF rarely had pain after manually touching the area around the vaginal introitus. She rarely required external lubrication and was able to become lubricated during sexual activity most of the time. PF experienced orgasms most of the time. She felt sexual desire about once a week or less but always got aroused during sexual activity, yet she sometimes felt distressed about her sexual life.

After one month of using 5% GTO, her discomfort became mild was confined to the outer edges, at 3 o'clock and 9 o'clock of the vaginal introitus and she no longer had pain or discomfort during vaginal penetration. PF rarely required external lubrication and now she always became self-lubricated during sexual activity and continued to experience orgasms most of the time. PF felt sexual desire still about once a week or less and still always got aroused during sexual activity and seldom felt distressed about her sexual life. She felt that the medication was effective and that she had significantly less discomfort than she had before using the medication. She had no adverse effects from the medication. "Definitely more effective than estrogen cream daily regime, good for compliance." Her only concern was her ability to have access to the medication after the study was over.

Female Sexual Function Index (FSFI) for PF:

|  | BEFORE | AFTER |
| --- | --- | --- |
| Desire | 3.6 | 3.6 |
| Arousal | 4.8 | 5.7 |
| Lubrication | 5.1 | 6.0 |

-continued

|  | BEFORE | AFTER |
| --- | --- | --- |
| Orgasm | 4.8 | 5.6 |
| Satisfaction | 3.6 | 6.0 |
| Pain | 2.8 | 5.2 |
| Total | 24.7 | 32.1 |

A score of <=26.55 is diagnostic of female sexual dysfunction. The patient had female sexual dysfunction before using the study medication that resolved after using the medication for one month. In fact, she began to notice a decrease in pain after 5 days of daily use. She had no adverse effects. Of note was the particular and significant increase in satisfaction accompanied by a decrease in pain.

Patient Global Patient Global Impression of Improvement: scored the highest with "Very much improved"

Patient Benefit Evaluation: "Overall do you believe that you have experienced a meaningful benefit from the study medication?" Answer: Yes.

Sexual Activity Log (SAL)

Prior to using the 5% GTO, the subject had a moderate desire that was maintained throughout the study period. PF had one sexual activity in the prior week to using GTO because "would be too sore" (to have more). After using the medication every day for a month she had two sexual activities during the week prior to filling out the questionnaire that were satisfying. This log was not taken each week because patient's partner travels for weeks at a time and travels internationally.

Sexual Distress Scale Revised

A score of >11 is indicative of Female Sexual Distress. Prior to use of the study medication subject had a score of 16 qualifying her as having Sexual Distress. After one month of use of the medication she had a score of 4. She was no longer distressed by her sexual function. Item #13 pre: 0 (never) post: 0 (never)

The Vulvovaginal Symptom Questionnaire:

The subject's distress decreased on this questionnaire from before score of 4/21 to 0/21 afterwards. Of note, she had vulvar pain before use of medication and not after one month of using 5% GTO 4. Patient AM Presenting Complaint: AM was a 48-year-old pre-menopausal woman with complains of Genitopelvic pain/penetration disorder (GPPD) manifesting as vestibulodynia and pain inside her vagina during intercourse, dyspareunia.

Benefit realized: After one month of using 5% GTO AM noticed significant decrease in her vulvar/vaginal pain, dyspareunia. (GPPD) She noted an unexpected increase in her sexual desire and in the intensity and number of orgasms that she experienced as "greatly enhanced". She continues to use 5% GTO on a daily basis for at least 7 months after conclusion of the study.

Medications: Celebrex prn

Patient is a 48-year-old Italian Caucasian medium complexion premenopausal women with regular menses in a long term relationship who, for more than 10 years, had "occasionally" felt "moderate" "throbbing or soreness" in her vagina at the introitus and inside during vaginal penetration. She was able to become lubricated "most of the time" during sexual activity. AM experienced orgasm "most of the time," but only "sometimes" during sexual activity with her partner. Intercourse was the activity that provoked the discomfort or pain i.e. dyspareunia. She "sometimes"

felt discomfort after intercourse. She felt desire "occasionally, once a week or less" and was aroused "most of the time" during sexual activity. AM "sometimes" felt distress about her sexual life. Discomfort "somewhat" affected her sexual life, but it was not the only reason she would not be sexually active.

After one month of daily application of 5% GTO, she "almost never" experienced discomfort during vaginal penetration. AM continued to maintain her level of lubrication as "most of the time." She continued to orgasm "most of the time" which now included "most of the time" during sexual activity with her partner. Now she "rarely" felt discomfort after intercourse. Her sexual desire increased to "often, several times a week," and was aroused "most of the time" during sexual activity. AM "seldom" felt distressed about her sexual life. Discomfort "no longer had an effect on her sexual life" as it was now only intermittent. For this patient, the overall decrease in pain and increase in sexual desire that she experienced were the main reasons for her improved satisfaction with her sexual life after using the 5% GTO. She noted an unexpected increase in the intensity and number of orgasms that she was able to experience on more than one occasion during partner sexual activity. During routine daily life after several weeks of using 5% GTO she noted an "awareness of feeling pleasure stirring, sexual sensations from my groin and (pelvic) area."

Patient Benefit Evaluation: "Overall do you believe that you have experienced a meaningful benefit from the study medication?" Answer: Yes Patient Global Impression of Improvement: scored the highest with "Very much improved." AM reported significantly less discomfort than before using study medication.

Female Sexual Function Index (FSFI) for AM:

|  | BEFORE | AFTER |
| --- | --- | --- |
| Desire | 3.6 | 4.8 |
| Arousal | 4.5 | 5.4 |
| Lubrication | 5.1 | 6.0 |
| Orgasm | 4.4 | 6.0 |
| Satisfaction | 4.8 | 6.0 |
| Pain | 4.4 | 6.0 |
| Total | 26.8 | 34.2 |

A score of <=26.55 is diagnostic of female sexual dysfunction. Patient did not meet criteria for Female sexual dysfunction diagnosis by only 0.25, yet still derived a significant improvement in her overall sexual function.

Sexual Activity Log (SAL)

Prior to use of 5% GTO, patient's most intense level of sexual desire was "low desire" after 3 weeks of use it was "moderate" after 4 weeks she rated her most intense level of sexual desire as "strong." AM went from "moderately" distressed about her level of desire prior to use of 5% GTO to "a little bit" after one week's use to "not at all" by end of three weeks and maintained "not at all" after 4 weeks. Her incidence of sexual activity prior to use of 5% GTO increased throughout the study period. She reported 2 episodes of sexual activity prior to the study, 1 after first week, 2 after third week to 3 at the end of the fourth week. At all times, she rated her sexual activity as satisfying with orgasms. AM noted, with great enthusiasm, that she experienced several intense orgasms during sexual activity partner during the fourth week. In sum her desire increased and any distress that she had prior to use of 5% GTO was eliminated.

Sexual Distress Scale Revised

A score of >11 is indicative of Female Sexual Distress. Pre GTO score was 20 Post GTO score was 10. Her score before qualified as sexual distress. After using 5% GTO she no longer qualified as having sexual distress. The decrease in her discomfort/pain was notable as well as increase in orgasmic intensity.

The Vulvovaginal Symptom Questionnaire

She reported no complaints in skin of the vulva before or after using study medication. Her problem was more inside the vagina at the entrance.

5. Patient DI

This patient illustrates that a woman with sensitive skin may need to use 5% GTO less often (2-3 times per week) until a tolerance is built up frequency of usage can increase to optimize therapeutic effects.

Presenting Complaint: Genitopelvic pain disorder dyspareunia secondary to post-menopausal VVA, vulvodynia Vaginal Maturation Index Pre 5% GTO: 10% parabasal cells, 90% intermediate cells; 0% superficial cells Vaginal Maturation Index Post5% GTO: 100% parabasal cells Benefit of 5% GTO (3x/week) Genitopelvic pain vulvodynia and dyspareunia improved as did lubrication Preexisting conditions: hypothyroid, anxiety Medications: citalopram; Synthroid; 5% GTO Patient is a 66-year-old fair complexion sensitive skin German descent Caucasian female initially had improvement after one week of using 5% GTO then became irritated and stopped using the medication. After a few weeks of using her old formula of a Vitamin E suppository, which she did not like because it leaked and was messy, she returned to 5% GTO twice a week without a problem and with noticeable improvement in her dryness and discomfort due to lack of lubrication. DI classified herself as "very sensitive" skin. She did not fit the designated study period of one month with regular daily use of the medication. Initial period of use (interrupted by a few weeks) was approximately 6 months.

Afterward, patient was able to increase her use of 5% GTO to every other day avoiding irritation.

DI was an early entrant into the study and was only given one of the questionnaire forms as the other forms were not prepared and issued until later.

Vaginal maturation index was moderate with 10% parabasal cells; 90% intermediate and 0% superficial cells. Vaginal pH was 6.0. Upon repeat in October she had 100% parabasal cells indicating no estrogenic effects of the 5% GTO use at 2 times per week.

Patient is a 66-year-old female 10 years post-menopausal woman who prior to the use of GTO had experienced "one to five years" of "severe" "burning, soreness and cramping" "some of the time" during either "intense exercise or intercourse". This pain was located on her entire vulvar area from the inside of her labia minora to the vaginal introitus. She experienced mild discomfort sometimes however during vaginal penetration, pain occurring only when areas where touched or rubbed. She never became lubricated and always used a vaginal lubricant. She experienced orgasm most of the time. The pain "somewhat" affected her sexual life.

Initially, DI was started on 15% GTO that proved to be very irritating so she stopped using the medication and went back to using her Vitamin E suppository despite it being cumbersome. Five months after her initial evaluation the patient was restarted on 5% GTO and was able to use it two to three times per week without irritation. Her discomfort now "mild" and only "occasional" with direct contact with areas located in a more confined area to the posterior forchette and the lateral edges of the vaginal introitus. DI no longer had pain during vaginal penetration. She still never became lubricated. She experienced orgasm most of the time including during partner sexual activity. She rarely experienced pain or discomfort during vaginal penetration. She "rarely" felt distress about her sexual life. Overall, patient went from having severe pain to no pain or discomfort in her vulva enabling her to have an overall improvement in her sexual life. She felt that the medication was " . . . extremely effective. I no longer experience any discomfort or pain. It (5% GTO) has been life changing. I felt that I had interstitial cystitis when in reality it was vaginal dryness. Now I no longer have any urinary tract issues!"

Patient Benefit Evaluation: "Overall do you believe that you have experienced a meaningful benefit from the study medication?" Answer: Yes Patient Global Patient Global Impression of Improvement: Her vulvodynia resolved and she maintained a higher level of lubrication scoring the highest with "very much improved" She reported significantly less discomfort than before using study medication.

Female Sexual Function Index
AFTER USE OF 5% GTO

|  |  |
|---|---|
| Desire | 3.0 |
| Arousal | 4.2 |
| Lubrication | 1.2 |
| Orgasm | 4.8 |
| Satisfaction | 4.8 |
| Pain | 5.6 |
| Total | 23.6 |

A score of <=26.55 is diagnostic of female sexual dysfunction Patient continued to meet the criteria for female sexual dysfunction despite an improvement in her symptoms. She verbally noted an increase in lubrication and a decrease in pain.

Sexual Distress Scale Revised: A score of >11 is indicative of Female Sexual Distress. Patient reports a 6 thus is not distressed over her level of sexual function after using the 5% GTO. However, there is no pre test data to compare this to for this patient. This patient was "never" bothered by her lack of sexual desire. There was no apparent increase in her sexual desire with every other day use of 5% GTO over several months.

The Vulvovaginal Symptom Questionnaire: Patient still has symptoms using the 5% GTO only 2 times per week with a score of 9/21. There is no pretest for this subject however because as an early entrant into the study not all questionnaires had been instituted. After continued use of 5% GTO over several months (which she now tolerated every other day) her score improved significantly and was 2/21 with resolution of pain and dryness. In sum, the patient's symptoms improved after she was able to use the correct lower percentage of GTO at a frequency she could tolerate without irritation. She continues to use GTO for over 9 months, renewing her medication.

There was a visible difference in the appearance of her vulva after using the medication only twice per week. This patient used the study medication two to three times per week. Daily use was not tolerated due to sensitivity and irritation. She had a nearly complete resolution of all symptoms after using 5% GTO.

6. Patient NS (control)
Presenting Complaints: NONE—was a control
Benefit of 5% GTO: decrease in genitopelvic pain and increased lubrication Patient is a 43-year-old Hispanic premenopausal female without any complaints serving as a control.

Vaginal pH was 5.5 before and after daily use of study medication for one month.

Medication: 5% GTO initially and 7.5% GTO subsequently
Test period: one month

Prior to use of the 5% GTO NS reported "almost never" any pain in her vulvovaginal area always became lubricated but always used a lubricant and always experienced an orgasm. Intercourse would provoke mild discomfort or pain described as "soreness or throbbing with muscle spasms (involuntary tightening of muscles in vagina)" which "had no effect on her sexual life." Her level of sexual desire was occasionally once a week or less There was no significant change after using the 5% GTO.

Patient Benefit Evaluation: "Overall do you believe that you have experienced a meaningful benefit from the study medication? She answered: YES that she had experienced a meaningful benefit from the study medication.

Patient Global Patient Global Impression of Improvement: scored the highest with "slightly improved" She reported "maybe, but I am not sure" medication helped relieve her discomfort.

Female Sexual Function Index

|  | BEFORE | AFTER |
|---|---|---|
| Desire | 4.2 | 3.6 |
| Arousal | 4.5 | 4.2 |
| Lubrication | 3.6 | 5.7 |
| Orgasm | 5.6 | 6.0 |
| Satisfaction | 6.0 | 6.0 |
| Pain | 3.2 | 4.8 |
| Total | 27.1 | 30.3 |

A score of <=26.55 is diagnostic of female sexual dysfunction

Patient did not meet the criteria for female sexual dysfunction but still had an improvement in her symptoms particularly in increase of lubrication and decrease in pain.

Sexual Distress Scale Revised: A score of >11 is indicative of Female Sexual Distress. Patient reports a 2 thus was not distressed over her level of sexual function prior to use of 5% GTO and 5 after using the 5% GTO. She continued not to suffer from distress over her sexuality. Item #13 pre 1 (rarely) post 1 (rarely)

The Vulvovaginal Symptom Questionnaire: Pre GTO score 3. Post GTO score 2. Pain was noted on the pre questionnaire but resolved after 4 weeks of daily use of 5% GTO. She still noted dryness despite use of medication.

Sexual Activities Log (SAL):
Patient had a "moderate" desire throughout the study period, was not at all distressed by her level of desire and had 3 episodes of sexual activity with orgasms each week. There was no change for this patient.

7 Patient LT:
Presenting Complaint: Genitopelvic pain/penetration disorder Pain (vulvadynia and dyspareunia.):
Benefit of 5% GTO: decrease in genitopelvic pain/penetration (vulvadynia and dyspareunia); increase arousal/desire; orgasm Side Effects: None
Medication: 5% GTO
Desire and Arousal BEFORE 8.1 AFTER 11.1
Genitopelvic pain/penetration disorder Pain 3.2 BEFORE 4.8 AFTER
SAL 0 BEFORE 7 AFTER
PmHx: GERD
Medications; 5% GTO Mobic, Nexium
Vaginal pH prior and post 5.5
Duration of medication use 3.2 weeks (did not use with menses)

This 48-year-old Iranian medium complexion dark haired pre-menopausal woman prior to use of the study medication had experienced greater than 10 years of "knife-like cutting pain" only during intercourse or manual touching "most of the time" which was rated as "significant." The pain was located in a semicircle in the area of the posterior forchette of the vaginal introitus. LT "always" became lubricated during sexual activity and never required use of lubricant. She was able to have an orgasm "most of the time" but only "sometimes" during sexual activity with her partner. She "frequently" felt sexual desire about on a "daily" basis but was "constantly" distressed about her sexual life because of the provoked pain upon intercourse. "It affects my sexual life very much." The sensation of pain was the main reason why she would decline having intercourse despite feeling a sexual desire to do so.

After using the 5% GTO, she no longer had pain but "rarely" had a "mild" discomfort during intercourse or vaginal penetration but "never" during manual touching of the area outside her vagina. She was always able to become lubricated. She was able to have an orgasm "sometimes" during sexual activity with her partner. LT "frequently" felt sexual desire about on a "daily" basis and she "always" became aroused during sexual activity. She no longer had pain affecting her sexual life. She was "sometimes" distressed about her sexual life and the discomfort only affecting her sex life "somewhat." LT felt that the medication was "effective." "I no longer experience pain or discomfort." She had no adverse side effects from the medication and no problems using the medication. "Before using the medication I didn't have a desire to have sex, because of worrying about having pain, bleeding and swelling. I was stressed about being with someone. After using the 5% GTO, I had no pain, no swelling, and no bleeding. I was so comfortable. This medication changed my life. The best part was feeling close to my partner emotionally and physically."

Female Sexual Function Index (FSFI questionnaire) results after using 5% GTO were as follows:

|  | BEFORE | AFTER |
| --- | --- | --- |
| Desire: | 4.8 | 5.4 |
| Arousal | 3.3 | 5.7 |
| Lubrication | 5.7 | 5.7 |
| Orgasm | 3.6 | 4.0 |
| Satisfaction | 5.2 | 6.0 |
| Pain | 3.2 | 4.8 |
| TOTALS | 25.8 | 31.6 |

A score of <=26.55 is diagnostic of Female Sexual Dysfunction. Patient had female sexual dysfunction prior to using the study medication and her female sexual dysfunction resolved after using the 5% GTO without any adverse effects. Patient had a significant increase in several parameters, most notably in her sexual arousal, and decrease in pain.

Patient Global Impression of Improvement: "Improved".
Patient Benefit Evaluation: "Overall do you believe that you have experienced a meaningful benefit from the study medication?" Answer Yes.
Sexual Activity Log SAL:

Prior to using the study medication subject had "moderate" sexual desire for the week prior to using the medication. She was "quite a bit distressed about her level of sexual desire, yet had no sexual activity in the prior week and did not have an orgasm. At the end of four weeks of using the 5% GTO, LT experienced strong sexual desire, was not at all distressed about her level of desire, and had seven satisfying sexual events with orgasms in the prior week. She had her menses once during the testing period during which time she neither had intercourse nor used the medication.

She stated that she had no problems using the medication and no unpleasant side effects.
Sexual Distress Scale-Revised:

Prior to use of the study medication subject had a score of 7. After use of the medication she had a score of 7. There was no difference on this scale from before to after using the 5% GTO. Item #13 pre 1 (rarely) post 0 (never)
The Vulvovaginal Symptom Questionnaire:

The subjects distressed significantly decreased from a pre-GTO score of 5/21 to post-GTO score of 1/21 indicating lack of physical symptoms, emotional concerns, life impact, and sexual impact. Physical symptoms of hurting, irritation pain and bleeding resolved and were the reasons for this improvement.

8 Patient SW—Control
Presenting Complaints: None Control
Benefit of 5% GTO: None
Side Effects: None
Vaginal pH 5.5 before and after use of 5% GTO
Meds: Wellbutrin oral
Xanax 0.25 mg Oral—tablet
Vitamin D prescription 50,000 units twice a week Patient is a 38-year-old Italian Caucasian medium complexion premenstrual female with no complaints. She was asked to participate as a control. She had no pain, including during intercourse. She "always" became lubricated during sexual activity, never using a lubricant and experienced orgasm "most of the time." There was no change after using 5% GTO three of the four weeks (she had menses during the study). She had no problems or complaints about using the medication.

Female Sexual Function Index (FSFI questionnaire) results after using 5% GTO were as follows:

|  | BEFORE | AFTER |
| --- | --- | --- |
| Desire: | 3.6 | 4.8 |
| Arousal | 5.7 | 5.4 |
| Lubrication | 6.0 | 6.0 |
| Orgasm | 6.0 | 5.6 |
| Satisfaction | 6.0 | 6.0 |
| Pain | 6.0 | 6.0 |
| TOTALS | 33.3 | 33.8 |

Patient had no female sexual dysfunction prior to or after using the study medication. 5% GTO was used daily without any adverse effects. Patient did have an increase in her level of desire after using the 5% GTO. It is of interest that she "sometimes" felt "moderate" desire prior to use of 5% GTO but after use of 5% GTO for one month "most of the time" felt "high" desire. This was the ONLY change noted for this patient in any of the parameters or questionnaires.

Patient Global Impression of Improvement: "unchanged" in this control patient

Patient Benefit Evaluation: "Overall do you believe that you have experienced a meaningful benefit from the study medication?" Answer NO for this control patient Sexual Activity Log SAL:

She had her menses once during the testing period during which time she neither had intercourse nor used the medication. Her SAL was identical before and after use of the study medication indicating no effect in this control patient. She had "strong desire", no distress over her level of desire. She had three episodes of sexual activity that were satisfying and with orgasms the week prior to use of 5% GTO and the week after using 5% GTO for the preceding month, excluding week of menses.

She stated that she had no problems using the medication and no unpleasant side effects.

Sexual Distress Scale-Revised:

Prior to use of the study medication subject had a score of 0. After use of the medication she had a score of 0. There was no difference on this scale from before to after using the 5% green tea ointment in this control patient. Item #13 pre-GTO 0 (never) post-GTO 0 (never)

The Vulvovaginal Symptom Questionnaire:

The questionnaire is to determine the nature and effect of a woman's vulvovaginal symptoms. The subject's pre-GTO score of 0/21 to 0/21 post-GTO indicated lack of physical symptoms, emotional concerns, life impact, and sexual impact. 5% GTO had no effect on this control patient.

For this high functioning premenstrual woman with no complaints of sexual dysfunction, serving as a control, the 5% GTO did not have either positive or negative effects. She declined trying a slightly higher concentration of 7.5% GTO.

9. Patient MD

Presenting Complaint: Arousal/Desire disorder—
Benefit of 5% GTO: Arousal/Desire increased
Complaints of Decreased sexual desire
Medication: 5% GTO
Duration of use one month between evaluations Patient is a 60-year-old woman 12 years post-menopausal after using the 5% GTO for only a week described an unexpected increase in her sexual desire. "Great product, increases desire!" She "frequently, on a daily basis" felt sexual desire. Her only concern after finishing the study was that she would be able to obtain more of the 5% GTO so that she could continue using it on a regular basis. She had no side effects. She had no pain including during intercourse and was able to have an orgasm "most of the time". She sometimes had difficulty lubricating and used a lubricant during intercourse. "Great product—very pleasant and effective. I recommend it. Helps with lubrication and desire! Female Sexual Function Index (FSFI questionnaire) results after using 5% GTO were as follows:

| | BEFORE | AFTER |
|---|---|---|
| Desire: | 3.6 | 4.8 |
| Arousal | 4.2 | 4.8 |
| Lubrication | 4.5 | 4.8 |

| | BEFORE | AFTER |
|---|---|---|
| Orgasm | 5.2 | 5.6 |
| Satisfaction | 4.8 | 5.2 |
| Pain | 5.6 | 5.6 |
| TOTALS | 27.9 | 30.8 |

A score of <=26.55 is diagnostic of Female Sexual Dysfunction.

Sexual Distress Scale-Revised:

Prior to use of the study medication subject had a score of 16 (>11 is indicative of Female Sexual Distress). After use of the medication she had a score of 6. She no longer had sexual distress after using 5% GTO. Patient stated that she had a definite increase in her sexual desire. Item #13 pre: 2 (occasionally) Post: 1 (rarely)

The Vulvovaginal Symptom Questionnaire:

The questionnaire is to determine the nature and effect of a woman's vulvovaginal symptoms. The subject's pre score of 0/21 to 0/21. There was no change.

Patient Global Impression of Improvement: On scale 1-7; 1 "very much improved"

Patient Benefit Evaluation: "Overall do you believe that you have experienced a meaningful benefit from the study medication?" Answer: Yes SAL: Sexual Activity Log SAL:

Prior to using the study medication subject had "moderate" sexual desire for the week prior to using the medication. She was not distressed about her level of sexual desire, yet had one sexual activity in the prior week and an orgasm. This was the same after one week. However, by the end of two weeks of using the 5% green tea ointment she had "strong sexual desire", was not at all distressed about her level of desire and had one satisfying sexual events with orgasm in the prior week. This level of desire was maintained for the duration of the study.

10. Patient CD (Patient 1)

Presenting Complaints: Arousal/Desire disorder (decreased libido); Genitopelvic pain with dyspareunia secondary to vulvovaginal atrophy Benefit of 5% GTO: Arousal/Desire and genitopelvic pain
PmHx: hypothyroid
Meds: levothyroxine
Female Sexual Disorder of arousal and desire: Greatly improved enhanced libido.
SAL: 0 Before 1 After
Medication: 15% GTO Patient is a 56-year-old post-menopausal female and an initial trial study patient who only filled out forms on the first visit and was seen in the office for a follow up exam and discussion of her condition. She had thinning of her vulvar and vaginal epithelium, the vaginal introitus was somewhat firm and fibrous upon examination with her gynecologist, with a vaginal pH of 7 consistent with atrophic vaginitis. CD was given 15% GTO to use "a dab" once a day at night to vulvar area and one inch into vagina. She had not had any intercourse for six months because of lack of desire. After using the 15% green tea extract in ointment for 10 days to two weeks she developed an increase in libido and attempted to have intercourse but was unable to have complete penetration and was very uncomfortable trying to have intercourse due to secondary narrowing of the vaginal introitus. Further, intercourse was not possible because of pain at the introitus. CD did have other sexual relations despite inability to have vaginal intercourse. She experienced some discomfort over the next 24 hours but later returned to baseline. Patient was very happy to once again to have experienced sexual desire. She was instructed to use Vitamin E vaginal suppositories along with 5% GTO and a vaginal dilator to recondition her vaginal introitus to enable future intercourse. Patient was unavailable for follow up.

11. Patient LM

Presenting Complaint: Genitopelvic pain/dyspareunia secondary to atrophic vulvovaginal atrophy, lack of lubrication, possible LS &A and prolapse of vagina. Benefit of 5% GTO: Genitopelvic pain/dyspareunia improved significantly as did lubrication. The efficacy of 5% GTO for lubrication was comparable to Estring 2 mg vaginal ring in this patient.

Patient is a 67-year-old woman, 12 years post-menopausal, with a chief complaint of vaginal dryness and "moderate" pain "soreness" inside her vagina and under her clitoris secondary to the dryness only during penetration or foreplay. She required lubrication "most of the time" and was "rarely" able to experience an orgasm. She only felt sexual desire "once a month not often." She "sometimes" felt distressed about her sexual life. Upon physical examination she had some prolapse of her vagina (which was confirmed upon speaking to her gynecologist). She may also have some loss of labia minora. She had stopped her Estring 2 mg vaginal ring for one month prior to using the 5% GTO and was seeking out another way of ameliorating her dryness without the use of estrogens. She felt that the medication was effective because she had significantly less discomfort than before using the medication. LM had no discomfort during vaginal penetration although she continued to use a lubricant for intercourse. She was able to experience an orgasm with masturbation. She was able to substitute 5% GTO for her Estring and have same effect on her degree of lubrication. She wanted to continue to have access to the 5% GTO after the study ended.

Medications: Low Dose Aspirin oral; 5% GTO atorvastatin oral; Effexor XR oral; losartan oral acyclovir Duration between evaluations: one month Maturation index: before 100% intermediate cells (note patient had used Estring one month prior) pH 6.0. Post one month Nov. 18, 2015 of use of 5% GTO 100% Intermediate cells. This shows efficacy of the maturation index test. This woman was using estrogens even though post-menopausal so see effect of estrogens on vaginal maturation index didn't change in one month. Female Sexual Function Index (FSFI questionnaire) results after using 5% green tea ointment were as follows:

|  | BEFORE | AFTER |
| --- | --- | --- |
| Desire: | 1.8 | 1.8 |
| Arousal | 2.4 | 2.7 |
| Lubrication | 2.1 | 4.8 |
| Orgasm | 1.2 | 2.0 |
| Satisfaction | 2.4 | 3.2 |
| Pain | 3.6 | 6.0 |
| TOTALS | 13.5 | 20.5 |

A score of <=26.55 is diagnostic of Female Sexual Dysfunction. Prior to use of the study medication subject had a score of 13.5. After use of the medication she had a score of 20.5. Her increase in lubrication and consequent decrease in pain accounted for the improvement in her sexual dysfunction.

Sexual Distress Scale-Revised:

A score of >11 is indicative of Female Sexual Distress. Her score was 27 prior to use of 5% GTO and 23 after the use of the medication. Item #13 pre (3 frequently) post: (2 occasionally)

The Vulvovaginal Symptom Questionnaire:

The questionnaire is to determine the nature and effect of a woman's vulvovaginal symptoms. The subject's pre-score of 1/21 to 0/21 dryness was the one symptom that she reported before, which then resolved after use of the 5% GTO.

Patient Global Impression of Improvement: On scale 1-7 3 "improved"

Patient Benefit Evaluation: "Overall do you believe that you have experienced a meaningful benefit from the study medication?" Answer: Yes. "Improvement was increased vaginal lubrication."

Sexual Activity Log SAL:

Prior to using the study medication subject had low sexual desire for the week prior to using the medication. She was "a little bit distressed" about her level of sexual desire, yet had one sexual activity in the prior week and. this did not significantly change by the end of the fourth week except that she was not at all distressed.

12. Patient MP

Presenting Complaint: Genitopelvic pain/dyspareunia; vestibulodynia

Benefit of 5% GTO: Genitopelvic pain; patient had an increase in her desire but due to marital strife no sexual activity invalidated assessment of arousal/desire and orgasm This patient therefore was not included in statistical analyses.

Subject is a 52-year-old women who years prior had a hysterectomy but retained her ovaries who was experiencing menopausal symptoms of vulvovaginal atrophy, dyspareunia and vestibulodynia for the past one to five years. She always had discomfort of pain of moderate severity located in the entire area of the vulva inside her labia minora and particularly in the posterior forchette characterized by burning, throbbing, and soreness. After four weeks of use 5% GTO she had no longer had any pain or discomfort. She was able to become lubricated most of the time and only rarely needed external lubricant before use of the 5% GTO and after use never used lubricant. Before the use of the 5% GTO she occasionally felt sexual desire, (once a week or less) after 4 weeks of use she often (several times a week) felt sexual desire. Before the use of 5% GTO she frequently felt distressed about her sexual life but after using 5% GTO for 4 weeks she seldom this distress. "Very soothing to area. Have not experienced burning or itching on the overall area."

Medications: amitriptyline 5% GTO

Maturation Index Prior 10% parabasal cells; 85% Intermediate cells; 5% superficial cells pH Prior 5.5

Maturation Index Post: 20% parabasal cells; 80% Intermediate cells; 0% superficial cells pH Post 5.5

Female Sexual Function Index (FSFI questionnaire) results after using 5% green tea ointment were as follows:

|  | BEFORE | AFTER |
| --- | --- | --- |
| Desire: | 3.6 | 4.8 |
| Arousal | 4.8 | 1.8 |
| Lubrication | 5.4 | 5.4 |
| Orgasm | 5.2 | 3.9 |

-continued

|  | BEFORE | AFTER |
|---|---|---|
| Satisfaction | 3.6 | 1.2 |
| Pain | 1.6 | 6.0 |
| TOTALS | 24.2 | 23.1 |

A score of <=26.55 is diagnostic of Female Sexual Dysfunction. Prior to use of the study medication subject had a score of 24.2. After use of the medication she had a score of 23.1. She had experienced interpersonal marital difficulties during the study period which influenced her responses to arousal and satisfaction. She was dissatisfied with her personal relationship with her spouse. However, there was a marked decrease in her symptoms of pain from 1.6 to 6.0. A requirement of the study is that patients have an ongoing personal sexual relationship throughout the study period. Therefore, her values were not included in the statistical analysis of the FSFI. This patient did not despite significant improvement in her pain and desire.

Sexual Distress Scale-Revised:

A score of >11 is indicative of Female Sexual Distress. Her score was 25 prior to use of 5% GTO and 13 after the use of the medication. There was a significant improvement in her sexual distress score after using 5% GTO. Item #13 (pre: 0 never post: 2 occasionally)

The Vulvovaginal Symptom Questionnaire:

The questionnaire is to determine the nature and effect of a woman's vulvovaginal symptoms. The subjects pre-GTO score of 11/21 to post GTO score of 0/21 pain was the one symptom that she reported before and which then resolved after use of the 5% GTO Patient Global Impression of Improvement: On scale 1-7: 3 "improved."

Patient Benefit Evaluation: "Overall do you believe that you have experienced a meaningful benefit from the study medication?" Answer: Yes "Improvement was increased vaginal lubrication."

SAL: Sexual Activity Log SAL:

Prior to using the study medication subject had low sexual desire for the week prior to using the medication. She was "a little bit distressed" about her level of sexual desire, yet had one sexual activity in the prior week. Because of difficulty in her personal relationship with her spouse she did not have sex after the first week of the study. This patient did not masturbate or engage in non-coital sexual activity.

13. Patient MS

Presenting Complaint: Genitopelvic pain disorder with dyspareunia secondary to vulvovaginal atrophy.

Benefit of 5% GTO: resolution of Genitopelvic pain, dyspareunia and increase in lubrication.

Medications: Crestor oral; felodipine oral; Hyzaar oral.

Maturation Index pre-GTO: 50% parabasal cells; 40% Intermediate cells; 10% superficial cells pH Pre-GTO: 6.6

Maturation Index post-GTO: 100% parabasal cells;

pH Post 6.0

Duration between evaluations: one month

Patient is a 68-year-old woman 15 years post-menopausal with greater than ten years of complaints of "always" having "moderate" "sandpapery," "soreness" pain in the area of the posterior forchette of the vaginal introitus and inside her vagina which precluded any vaginal penetration including intercourse because of significant pain. She "sometimes" became lubricated during sexual activity but always used a lubricant. The pain was "absolutely the main reason" that she was not sexually active with her husband. After one month of daily use of 5% GTO only "some of the time" did she have "mild" discomfort during vaginal penetration. She had no pain after penetration. She became lubricated "most of the time" during sexual activity and only "sometimes" used a lubricant. Discomfort now only "somewhat" affected her sexual life. She felt that the medication was somewhat effective, she still experienced some discomfort but it was much improved. She had no problems or unpleasant side effects using the medication. "Felt lubrication before penetration which was very comfortable; for the past 13 years not able to have intercourse. Now I am able to have digital penetration without discomfort. I didn't think this was going to work but it really did."

Female Sexual Function Index (FSFI questionnaire) results after using 5% GTO were as follows:

|  | BEFORE | AFTER |
|---|---|---|
| Desire: | 1.8 | 1.8 |
| Arousal | 5.7 | 5.7 |
| Lubrication | 4.2 | 6.0 |
| Orgasm | 6.0 | 5.2 |
| Satisfaction | 6.0 | 5.2 |
| Pain | 0.0 | 6.0 |
| TOTALS | 23.7 | 29.9 |

A score of <=26.55 is diagnostic of Female Sexual Dysfunction. Prior to use of the study medication subject had qualified for female sexual dysfunction with a score of 23.7. After use of the study medication, she no longer had sexual dysfunction with a score of 29.9. Most notably, she had increase in her lubrication 4.2 to 6.0 and a significant decrease in pain from 0.0 to 6.0 in her score.

Sexual Distress Scale-Revised:

A score of >11 is indicative of Female Sexual Distress. Her score was prior to use of 5% GTO was 9 (nine) and 1 (one) after the use of the medication. There was a significant improvement in her sexual distress score after using 5% GTO.Item #13 pre: (3 frequently) post: (0 never)

The Vulvovaginal Symptom Questionnaire:

The questionnaire is to determine the nature and effect of a woman's vulvovaginal symptoms. The subject's pre score of 5/21 to 0/21 pain was the one symptom that she reported before and which then resolved after use of the 5% GTO.

Patient Global Impression of Improvement: On scale 1-7: 3 "improved"

Patient Benefit Evaluation: "Overall do you believe that you have experienced a meaningful benefit from the study medication?" Answer: Yes. "Improvement was increased vaginal lubrication and decreased pain"

SAL: Sexual Activity Log SAL:

The week prior to using the study medication, the subject had no sexual desire for the week prior to using the medication. She was "not at all distressed" about her level of sexual desire, yet had no sexual activity in the prior week. After 3 weeks of using 5% GTO, despite no change in desire, she had one satisfying sexual activity with an orgasm. By week 4 she had "low sexual desire" and one satisfying sexual activity with orgasm.

14. Patient SF

Presenting complaint: Genitopelvic pain (dyspareunia)

Benefit of 5% GTO: Genitopelvic pain (dyspareunia)

Orgasmic Disorders; Sexual interest Arousal Disorders
Vaginal Maturation index Pre: 100% superficial cells
Medications: Zocor, Forteo (Subcutaneous) Dexilant, Synthroid
Patient is a 52-year-old woman two to three years postmenopausal was referred by her gynecologic nurse practitioner. She always experienced "very significant," burning, throbbing, knife like cutting, soreness pain/discomfort, in the area of the posterior forchette, for the past 1-5 years during vaginal penetration which affected her sexual life "very much". She "frequently" felt distressed about her sexual life. She "rarely" became lubricated and "always" required external lubricant, only "sometimes" became aroused during sexual activity only "rarely" experiencing an orgasm. She "seldom" felt sexual desire and "frequently" felt distressed about her sexual life which. After using 5% GTO 2-3 times per week, (using it more often would irritate her) she still experienced pain/discomfort only now "most of the time" during intercourse but now it was "moderate" and now she "sometimes" became lubricated during intercourse, "most of the time" becoming aroused during sexual activity" experiencing an orgasm "sometimes". Patient noted an improvement after 2 weeks which was maintained for the duration of the study period. Her main improvement was in increased lubrication, increase in arousal and orgasm, and decreased pain. She still felt "frequently" distressed about her sexual life.

Female Sexual Function Index (FSFI questionnaire) results after using 5% green tea ointment were as follows:

|  | BEFORE | AFTER |
| --- | --- | --- |
| Desire: | 1.2 | 2.4 |
| Arousal | 1.2 | 3.6 |
| Lubrication | 0.3 | 3.0 |
| Orgasm | 0.0 | 4.8 |
| Satisfaction | 0.8 | 4.8 |
| Pain | 0.0 | 2.8 |
| TOTALS | 3.5 | 21.4 |

A score of <=26.55 is diagnostic of Female Sexual Dysfunction. Prior to use of the study medication subject had qualified for female sexual dysfunction with a score of 3.5 After use of the medication despite still meeting standard for having sexual dysfunction she remarkably improved with a score of 21.4. Most notably she had increase in her all categories especially in satisfaction, orgasm, and lubrication.

Sexual Distress Scale-Revised:
A score of >11 is indicative of Female Sexual Distress. Her score was prior to use of 5% GTO was 35 and after the use of the 5% GTO medication it was 29. There was a significant improvement in her sexual distress score afterwards.

Efficacy and effectiveness of certain aspects of the present invention may be better understood by consideration of the statistical analysis in the figures which compares the results observed in the above patient trials with the FDA study results of Flibanserin.

Figure 4A:
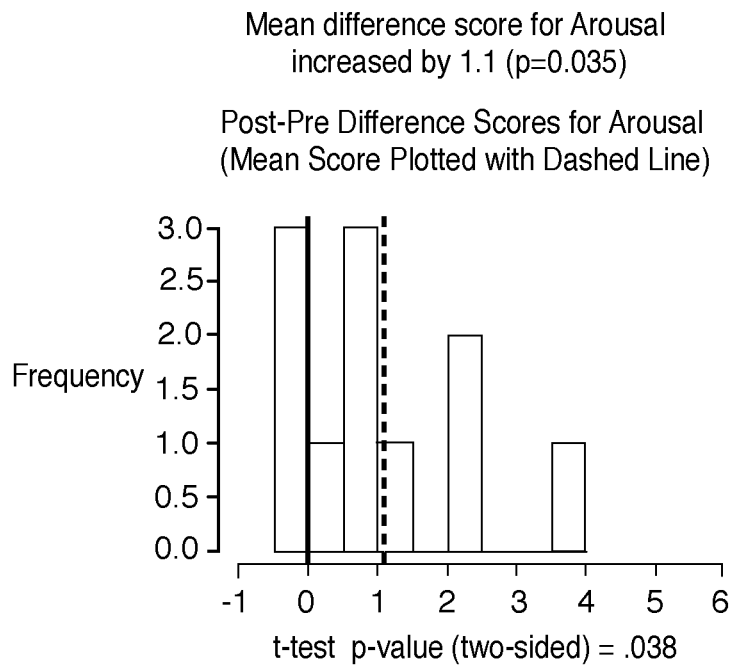
FIG. 4A is a statistical analysis of the increased arousal resulting from use of the catechin compositions of the invention.

FIG. 4A illustrates mean difference in arousal scores compared to the test subjects prior to treatment. As can be seen, users of the present invention are more likely to experience increased arousal. Compounds of the present invention resulted in a mean difference increase of 1.1 ($p=0.035$) in the FSFI arousal score.

Figure 4B:
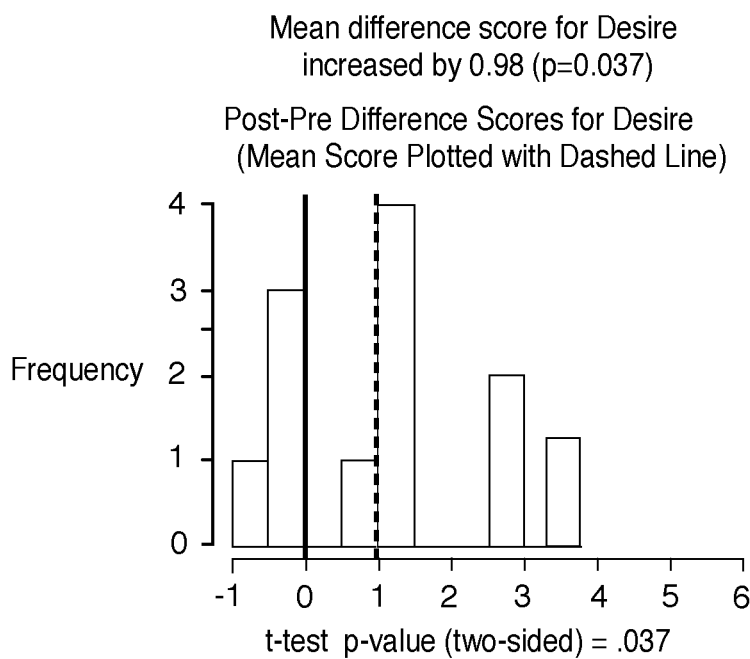
FIG. 4B is a statistical analysis of the increased desire resulting from use of the catechin compositions of the invention.

FIG. 4B illustrates mean difference in desire scores compared to the test subjects prior to treatment. As can be seen, users of the present invention are more likely to experience increased desire. Compounds of the present invention resulted in a mean difference increase of 0.98 ($p=0.037$) in the FSFI desire score.

Figure 4C:
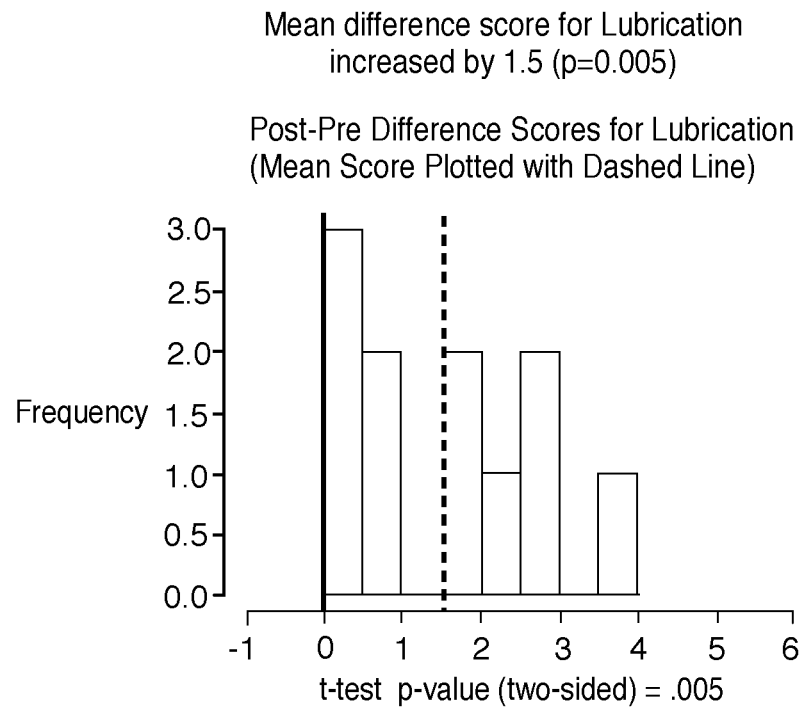
FIG. 4C is a statistical analysis of the increased lubrication resulting from use of the catechin compositions of the invention.

FIG. 4C illustrates mean difference in lubrication scores compared to the test subjects prior to treatment. As can be seen, users of the present invention more likely to experience increased lubrication. Compounds of the present invention resulted in a mean difference increase of 1.5 ($p=0.005$) in the FSFI lubrication score.

Figure 4D:
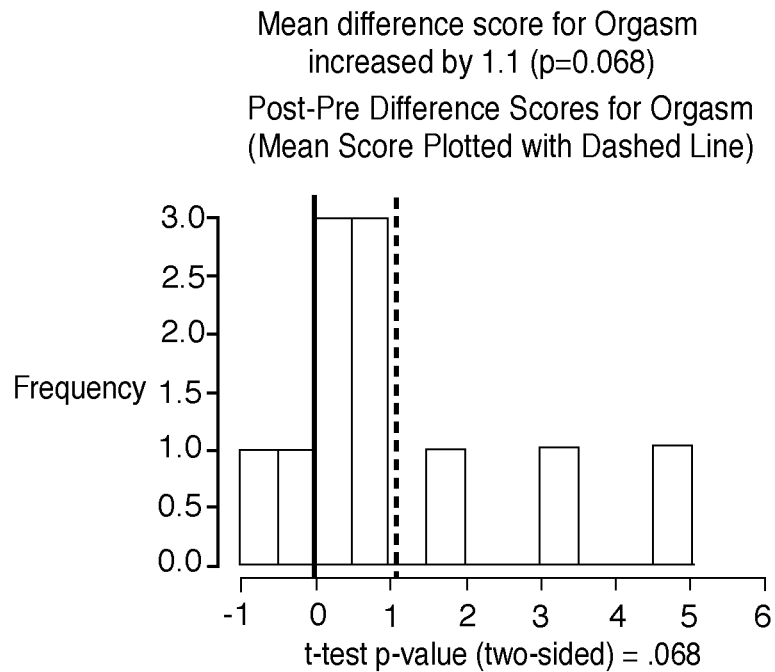
FIG. 4D is a statistical analysis of the increased orgasm resulting from use of the catechin compositions of the invention.

FIG. 4D illustrates mean difference in orgasm scores compared to the test subjects prior to treatment. As can be seen, users of the present invention more likely to experience an orgasm. Compounds of the present invention resulted in a mean difference increase of 1.1 ($p=0.068$) in the FSFI orgasm score.

Figure 4E:
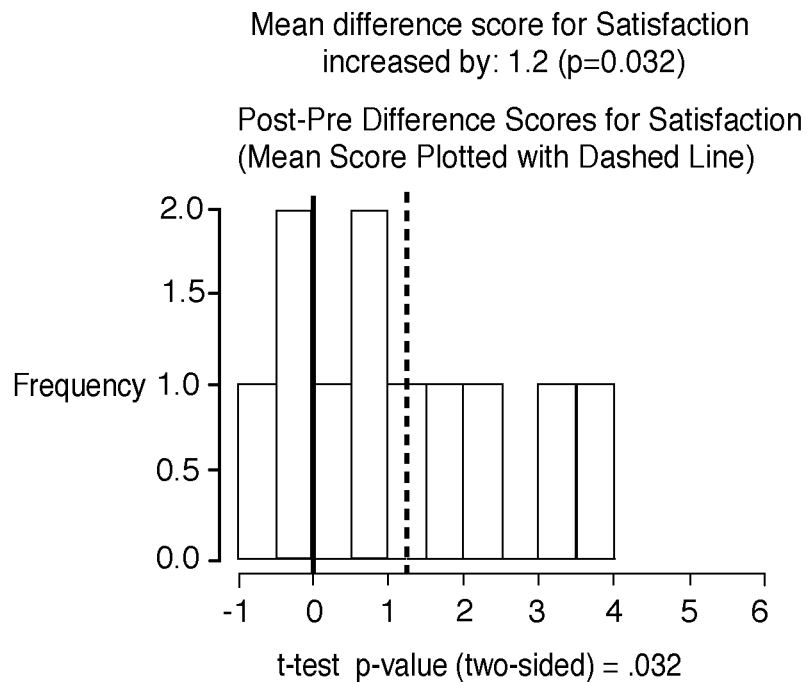
FIG. 4E is a statistical analysis of the increased satisfaction resulting from use of the catechin compositions of the invention.

FIG. 4E illustrates mean difference in satisfaction scores compared to the test subjects prior to treatment. As can be seen, users of the present invention more likely to have a satisfying sexual experience. Compounds of the present invention resulted in a mean difference increase of 1.2 ($p=0.032$) in the FSFI sexual satisfaction score.

Figure 4F:
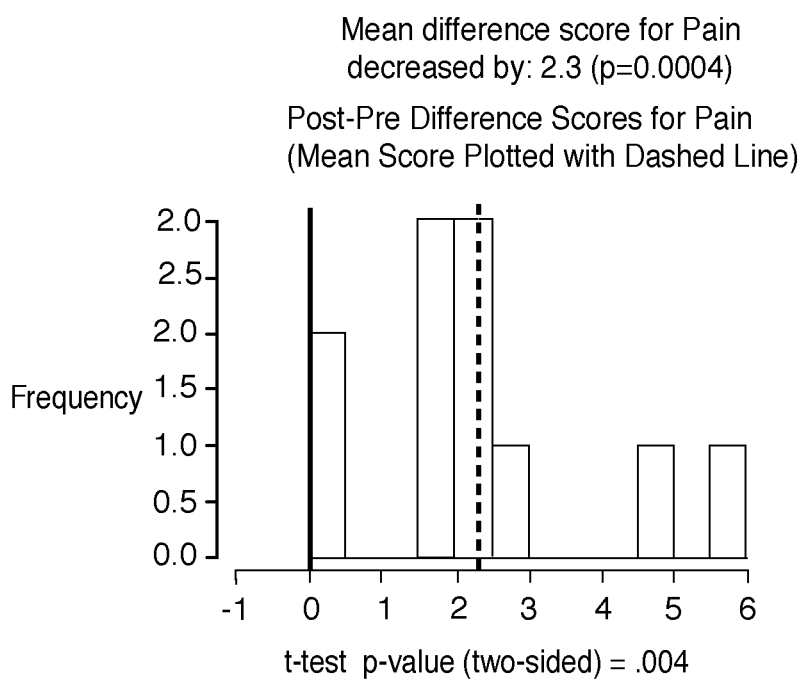
FIG. 4F is a statistical analysis of the decreased pain resulting from use of the catechin compositions of the invention.

FIG. 4F illustrates mean difference in pain scores compared to the test subjects prior to treatment. As can be seen, users of the present invention are less likely to have pain during a sexual experience. Compounds of the present invention resulted in a mean difference decrease of 2.3 ($p=0.0004$) in the FSFI pain score.

Figure 4G:
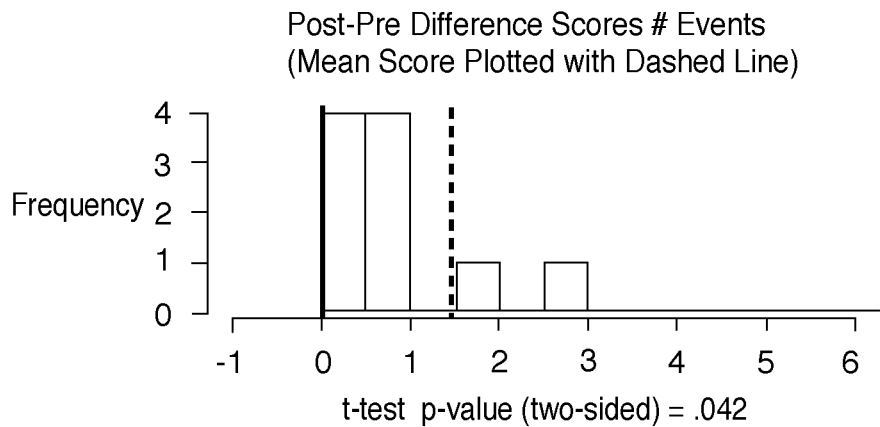
FIG. 4G is a statistical analysis of the increased satisfactory sexual events resulting from use of the catechin compositions of the invention.

FIG. 4G illustrates mean difference in Sexual Activities Log of Satisfying Sexual Events (SSE) scores compared to the test subjects prior to treatment. As can be seen, users of the present invention are more likely to have a satisfying sexual experience. Compounds of the present invention resulted in a mean difference increase score of 1.5 ($p=0.042$) in the SSE score.

Figure 4H:
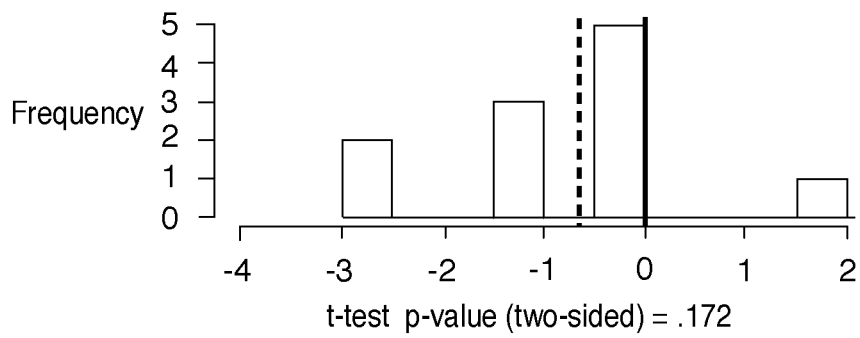
FIG. 4H is a statistical analysis of the decreased sexual distress resulting from use of the catechin compositions of the invention.

FIG. 4H illustrates the mean difference in the sexual distress scores (Item #13 in the Sexual Distress Score-Revised), of the test subjects post and prior to treatment. As can be seen, users of the present invention, although not reaching level of significance, trended to be less likely to experience sexual distress. Compounds of the present invention resulted in a mean decrease of −0.6 ($p=0.172$) in the sexual distress score.

Thus, as can be seen from the foregoing, topical application of Green Tea Ointment (GTO) in accordance with aspects of the present invention demonstrates clinical efficacy for premenopausal and postmenopausal women by decreasing genitopelvic pain disorder (GPPD) including during penetration, increasing sexual interest and arousal or alleviating symptoms of SIAD, and enhancing orgasm intensity and/or frequency for symptoms of FOD. These therapeutic effects of GTO were demonstrated in women who applied topical GTO over a period of four weeks to their vulva and vaginal introitus with no significant side effects.

Topical GTO was shown to be efficacious in reducing or completely eliminating vestibulodynia, a common cause of dyspareunia in both premenopausal and postmenopausal women. This condition may be seen in 15% of all premenopausal women sometime in their lifetime. It is a cause of genital pain and dyspareunia in postmenopausal unrelated to vulvovaginal atrophy. Vestibulodynia is a challenging disorder and there has been no definitive treatment for this condition despite use of a range of treatments. The catechin preparations of the present invention are the first and only chemical compound known to effectively treat vestibulodynia in both premenopausal and postmenopausal women.

Vulvovaginal atrophy, also a cause of genital pain and dyspareunia, exerts a negative impact on the quality of life of fifty percent (50%) of all postmenopausal women. In contrast to topical or systemic estrogenic drugs, topical GTO was effective in reducing or eliminating genital pain and dyspareunia caused by vulvovaginal atrophy without causing changes in the vaginal maturation index or the vaginal pH. This is evidence that GTO has no apparent estrogenic effects and is therefore safe in women with risk of breast or other reproductive malignancies, and carries no risk of stroke, deep venous thrombosis or dementia.

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed is:

1. A composition for treating a female sexual disorder (FSD), the composition comprising a catechin component for topical application to an individual's vulvovaginal area, wherein said FSD is selected from the group consisting of genitopelvic pain disorder (GPPD), vulvovaginal atrophy (VVA), vestibulodynia, dyspareunia, sexual interest arousal disorder (SIAD), and female orgasmic disorder (FOD).

2. The composition of claim 1, wherein said catechin component is at a concentration of between about 1% and 20% weight per weight of total composition (w/w).

3. The composition of claim 2, wherein said catechin component concentration is between about 2.5% and 15% by weight per weight of total composition (w/w).

4. The composition of claim 3, wherein said catechin component concentration is between about 4% and 12% by weight per weight of total composition (w/w).

5. The composition of claim 1, wherein said catechin component is a tea catechin.

6. The composition of claim 1, wherein said catechin component comprises an epigallocatechin gallate (EGCg).

7. The composition of claim 1, wherein said composition further comprises a selective estrogen receptor modulator (SERM).

8. The composition of claim 7, wherein said SERM is ospemifene.

9. The composition of claim 1, wherein said composition is an ointment, a lotion, an emulsion, an aqueous solution, or a non-aqueous solution.

10. A composition for treating a Female Sexual Disorder (FSD), comprising a catechin component or a derivative thereof for topical application to an individual's vulvovaginal area, wherein said composition normalizes, restores, enhances or improves an innervation density in said individual's vulvovaginal area, wherein said FSD is selected from the group consisting of Genitopelvic Pain Penetration Disorder (GPPD), vulvovaginal atrophy (VVA), vestibulodynia, dyspareunia, Sexual Interest Arousal disorder (SIAD), and Female Orgasmic Disorder (FOD).

11. The composition of claim 10, wherein said catechin component comprises epigallocatechin gallate (EGCg).

12. The composition of claim 11, wherein said epigallocatechin gallate (EGCg) is at a concentration of at least about 50% of said catechin component by weight per weight of total composition (w/w).

13. The composition of claim 10, wherein said catechin component is at a concentration of between about 1 % and 20% weight per weight of total composition (w/w).

14. The composition of claim 10, wherein said catechin component concentration is between about 2.5% and 15% by weight per weight of total composition (w/w).

15. The composition of claim 10, wherein said catechin component concentration is between about 4% and 12% by weight per weight of total composition (w/w).

16. The composition of claim 10, wherein said catechin component comprises the chemical structure:

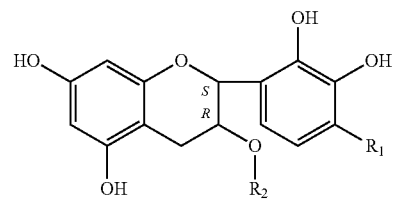

17. The composition of claim 16, wherein R1 is the chemical structure:

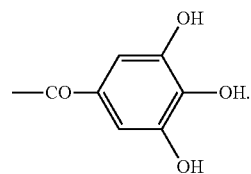

18. The composition of claim 10, wherein said composition further comprises a selective estrogen receptor modulator (SERM).

19. The composition of claim 18, wherein said SERM is ospemifene.

20. The composition of claim 10, wherein said composition is an ointment, a lotion, an emulsion, an aqueous solution, or a non-aqueous solution.

* * * * *